US011458269B2

(12) United States Patent
Hansmann et al.

(10) Patent No.: US 11,458,269 B2
(45) Date of Patent: Oct. 4, 2022

(54) DEVICE FOR VENTILATING A PATIENT AND PROCESS FOR THE OPERATION OF THE DEVICE

(71) Applicant: Drägerwerk AG & Co. KGaA, Lübeck (DE)

(72) Inventors: Hans-Ullrich Hansmann, Barnitz (DE); Nando Lüdtke, Hamburg (DE); Karsten Hiltawsky, Stockelsdorf (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 347 days.

(21) Appl. No.: 16/549,238

(22) Filed: Aug. 23, 2019

(65) Prior Publication Data

US 2020/0061319 A1 Feb. 27, 2020

(30) Foreign Application Priority Data

Aug. 24, 2018 (DE) ...................... 10 2018 006 699.2
Jul. 10, 2019 (DE) ...................... 10 2019 004 760.5

(51) Int. Cl.
*A61M 16/00* (2006.01)
*A61M 16/10* (2006.01)
(Continued)

(52) U.S. Cl.
CPC ...... *A61M 16/024* (2017.08); *A61M 16/0858* (2014.02); *A61M 16/106* (2014.02);
(Continued)

(58) Field of Classification Search
CPC ................ A61M 16/00; A61M 16/024; A61M 16/0816; A61M 16/085; A61M 16/0858;
(Continued)

(56) References Cited

U.S. PATENT DOCUMENTS 4,090,513 A * 5/1978 Togawa ............ A61M 16/1045
128/201.13
7,634,998 B1 12/2009 Fenley
(Continued)

FOREIGN PATENT DOCUMENTS

CN 102695536 A 9/2012
CN 204563192 U 8/2015
(Continued)

*Primary Examiner* — Joseph D. Boecker
(74) *Attorney, Agent, or Firm* — McGlew and Tuttle, P.C.

(57) ABSTRACT

A patient module (10) is intended for use when ventilating a patient with a pressure source (24) that can be fluidically coupled via the patient module (10) to a patient interface (26), which can be connected to the airways of a patient. The patient module (10) includes a housing (12) and a valve section (14) in the housing (12) as well as an HME filter (30) spaced apart from the valve section (14). The HME filter (30) is located upstream of the valve section (14) in relation to an expiratory volume flow, so that the HME filter (30) divides an interior of the housing (12) into a dry area and an area coming into contact with the moisture carried along by the exhaled breathing gas. The valve section (14) is located in the dry area. A process for operating the patient module (10) includes calibration steps.

23 Claims, 14 Drawing Sheets

(51) Int. Cl.
*A61M 16/20* (2006.01)
*A61M 16/08* (2006.01)

(52) U.S. Cl.
CPC ...... *A61M 16/107* (2014.02); *A61M 16/1045* (2013.01); *A61M 16/1065* (2014.02); *A61M 16/201* (2014.02); *A61M 16/204* (2014.02); *A61M 16/205* (2014.02); *A61M 2016/0027* (2013.01); *A61M 2016/0033* (2013.01)

(58) Field of Classification Search
CPC ............ A61M 16/1045; A61M 16/106; A61M 16/1065; A61M 16/107; A61M 16/201; A61M 16/204; A61M 16/205; A61M 2016/0027; A61M 2205/70
See application file for complete search history.

(56) References Cited

U.S. PATENT DOCUMENTS

| | | | | |
|---|---|---|---|---|
| 2007/0277825 | A1* | 12/2007 | Bordewick | A61M 16/16 128/204.23 |
| 2012/0097156 | A1* | 4/2012 | Bowman | A61M 16/06 128/201.13 |
| 2012/0138058 | A1* | 6/2012 | Fu | A61M 16/0069 128/204.23 |
| 2012/0152239 | A1 | 6/2012 | Shikani et al. | |
| 2013/0068219 | A1 | 3/2013 | Collazo et al. | |
| 2013/0190643 | A1* | 7/2013 | Brambilla | A61M 16/0069 600/543 |
| 2014/0276177 | A1* | 9/2014 | Brambilla | A61M 16/0666 600/543 |
| 2021/0290873 | A1 | 9/2021 | Fu et al. | |

FOREIGN PATENT DOCUMENTS

| | | | |
|---|---|---|---|
| CN | 204864416 U | 12/2015 | |
| CN | 106620978 A1 | 5/2017 | |
| DE | 4438216 A1 | 5/1995 | |
| DE | 102017009603 A1 | 4/2019 | |
| EP | 0841083 A1 | 5/1998 | |
| EP | 0856327 A2 * | 8/1998 | .......... A61M 16/085 |
| EP | 0856327 A2 | 8/1998 | |
| EP | 2065068 A1 | 6/2009 | |
| GB | 2430380 A | 3/2007 | |
| JP | H10111232 A | 4/1998 | |
| JP | H10211187 A | 8/1998 | |
| WO | 9732619 A1 | 9/1997 | |
| WO | 2019072606 A1 | 4/2019 | |

* cited by examiner

DEVICE FOR VENTILATING A PATIENT AND PROCESS FOR THE OPERATION OF THE DEVICE

CROSS REFERENCE TO RELATED APPLICATIONS

This application claims the benefit of priority under 35 U.S.C. § 119 of German Applications 10 2018 006 699.2, filed Aug. 24, 2018, and 10 2019 004 760.5, filed Jul. 10, 2019, the entire contents of each application are incorporated herein by reference.

TECHNICAL FIELD

The present invention pertains to a device for ventilating a patient, which is designated below as a patient module, and furthermore, it also pertains to a process for the operation of the patient module.

TECHNICAL BACKGROUND

Devices for ventilating a patient are, e.g., ventilators (also known as respirators) or anesthesia devices. Ventilators and anesthesia devices—designated below in summary as ventilators or simply as ventilator—are used to provide breathing air to patients, who either cannot breathe independently at all or need help with breathing.

For this purpose, the patients wear a face mask, which covers the mouth and nose, or a tube, which is inserted into the throat or trachea of the patient. Such a face mask, a tube or the like—designated below in summary as patient interface—are connected to the ventilator via at least one ventilation tube.

The pressure on the side of the ventilator is raised by means of the ventilator for inhalation in a manner also known per se to a predefined or predefinable set value for the airway pressure, namely to a value above the so-called alveolar pressure, i.e., the pressure within the patient's lungs. This pressure difference leads to a volume flow in the direction of the patient's lungs. The volume flow disappears when pressure equalization is reached. The process is reversed for exhalation and the pressure on the side of the ventilator is lowered towards the alveolar pressure, so that a volume flow is obtained from the patient's lungs until a pressure equalization is carried out here as well. A pressure control, a volume control and various hybrids with different limitations are known for such an operation of a ventilator. Valves on the input side and on the output side (inhalation valve, exhalation valve) are actuated and opened or closed in a defined manner during the operation of the ventilator in a manner that is, in principle, known per se.

DE 4438216 C2 shows a moisture and heat exchanger unit for a breathing device. A housing with a moisture and heat exchanger body and/or with a bacteria filter has two housing halves. One housing half is facing the airways of the patient, another housing half is in connection with an opening for supply of air. The two housing halves are configured as being mutually rotatable about a circular connection.

U.S. Pat. No. 5,848,590 A shows a filter assembly for filtering breathing air which shall be breathed through a tracheostomy. The filter assembly comprises a housing part and a filter part. The filter part can be moved within the housing into an inhalation position or exhalation position because of a resulting pressure difference over the filter part caused by the breathing. This mobility brings about a change in the breathing resistance.

EP 2065068 A1 shows a device, which provides a function for determining elevated deep-breathing resistances for a gas flow through a filter assembly. Optionally, a bypass hole makes possible a gas flow past the filter. The filter may be configured, for example, as a heat moisture exchange filter (HME).

WO 199732619 A1 shows a device for monitoring breathing parameters of a ventilation system with a treatment device arranged in a ventilation tube system, consisting of a filter and/or a heat and moisture exchanger. The breathing parameters can be obtained from a pressure difference over the flow resistance of the treatment device in comparison to a reference value by analyzing pressure and/or flow variables.

A device for ventilating a patient, which is already designated there as a patient module and can be easily replaced, is known from the older German application DE 10 2017 009 603.1 (application date: Oct. 13, 2017) and corresponding International Application publication WO 2019 072 606 (A1). The patient module is pneumatically connected to a pressure source, in particular to a medium pressure source. A pressurized gas cylinder or even a ventilator of the type mentioned in the introduction come into consideration as a pressure source. The patient module couples the pressure source fluidically to a patient interface, specifically a face mask or the like, that is connected or can be connected to the airways of a patient. The patient module described in the above-mentioned older application comprises at least one exhalation valve or optionally an exhalation valve and an inhalation valve. Provisions are made with regard to the valve or each valve for this valve] to comprise a valve drive intended for generating a control pressure in a control pressure chamber. A "micropump," in particular a piezo pump which can be operated under high frequency, acts as the valve drive. A control pressure that is generated by means of the piezo pump in the control pressure chamber determines a position of a closing element of the valve and the respective valve, i.e., the exhalation valve or inhalation valve is open or closed or partially open or partially closed depending on the position of the closing element.

With this reference and the above brief explanation, the above-mentioned older application DE 10 2017 009 603.1 and corresponding International Application Publication WO 2019 072 606 (A1) shall be considered to be included in the specification being submitted here with its full disclosure content, especially in relation to all explanations therein concerning the function and the operation of a piezo pump as well as concerning structural details of a piezo pump. In particular, each of DE 10 2017 009 603.1 and WO 2019 072 606 (A1) are incorporated herein by reference in their entirety.

An integration of a valve section with at least one exhalation valve or with at least one exhalation valve as well as at least one inhalation valve into a housing close to the patient (patient module) allows fast maneuvers during the ventilation, a measurement of physiological parameters close to the patient and/or a fast stabilization of spontaneous disturbance variables because of shorter time constants.

An integration of such a valve section into such a housing close to the patient must, however, take into account the conditions prevailing there, and especially the moisture prevailing there, as well as hygienic requirements.

SUMMARY

An object of the present invention is correspondingly to perfect a patient module known from the above-mentioned older application publication DE 10 2017 009 603.1 and publication WO 2019 072 606 (A1) at least in this regard.

This object is accomplished according to the present invention by means of a device for ventilating a patient, namely a patient module for use when ventilating a patient is placed under protection, wherein a pressure source can be fluidically coupled by means of the patient module to a patient interface that can be connected to the airways of a patient.

Provisions may be made in case of such a patient module intended for the fluidic coupling of a pressure source to a patient interface that can be connected to the airways of a patient for this patient module to comprise a housing and a valve section in the housing as well as at least one HME (Heat and Moisture Exchanger) filter, which is spaced apart from the valve section. As an alternative, the patient module may also have the at least one HME filter in the housing and possibly at least one particle filter, without the valve section being provided.

The (optional) valve section may comprise at least one exhalation valve or at least one exhalation valve as well as at least one inhalation valve.

With regard to a sequence of the valve section as well as of the HME filter within the housing, provisions may be made for the HME filter to be located upstream of the valve section in relation to an expiratory volume flow. In other words, the HME filter and the valve section are arranged in series, i.e., especially behind one another in relation to the flow sequence of the volume flow. Such a sequence guarantees that the expiratory volume flow and thus breathing gas exhaled by the patient reach the HME filter first and only after that the valve section within the patient module. The definition of the sequence of the valve section and of the HME filter with reference to the expiratory volume flow with the predefined flow direction thereof guarantees that the definition is independent of a later position (position in space) of the patient module during the application and the operation of the patient module.

One advantage of the present invention is that, on the one hand, an area that is "wet" and possibly loaded with microorganisms because of exhaled breathing gas during the operation and, on the other hand, and a "dry" area separated in space therefrom are formed in the interior of the housing of the patient module because of the HME filter located therein. The HME filter absorbs the moisture carried along by the exhaled breathing gas and stores this moisture.

During exhalation, the moisture carried along by the exhaled breathing gas thus does not reach beyond the HME filter, i.e., not in an area downstream of the HME filter. Additional advantages are associated with the "dry" area advantageously created in this manner in the interior of the housing of the patient module. These advantages pertain to the valve section and to a sensor mechanism or sensor arrangement comprised by the patient module or associated with the patient module.

The valve section comprised by the patient module is located in the dry area. Because of the valve section comprised by the patient module, the patient module is also a filter housing, which also comprises the actuator mechanism for controlling the inspiratory and expiratory breathing gas flows and which can be used close to the patient and is usually used close to the patient. The valve section comprises at least one exhalation valve, optionally at least one exhalation valve as well as at least one inhalation valve and a plurality of exhalation valves and at least one inhalation valve in case of a special embodiment. The valve or each valve comprised by the valve section is therefore likewise located in the dry area. This means that valve membranes or the like also remain dry and do not come into contact with the moisture carried long by the exhaled breathing gas. This maintains the operability of the valve or of each valve comprised by the valve section because wet valve membranes may, for example, stick or adhere to one another and thus may lead to different opening characteristics of a valve in comparison to a dry valve membrane.

A sensor mechanism of the patient module, for example, a pressure sensor or a plurality of pressure sensors, may also be located in the dry area of the housing of the patient module or be associated with this dry area.

Arrangement of the sensor mechanism in the dry area of the housing of the patient module avoids a contamination of the surface of the sensor mechanism and thus maintains the operability of the sensor mechanism. When the sensor mechanism is not located in the housing of the patient module, but is only associated with the dry area of the housing, there is such an association, for example, in the form of a tube or a plurality of tubes ending in the dry area and acting as supply lines, wherein the tube or each tube is coupled to a sensor, for example, to a pressure sensor (tube connection for pressure measurement) at the opposite end, so that the respective sensor is fluidically coupled by means of the tube to the dry area in the interior of the housing of the patient module. By a tube starting from an external sensor ending in the dry area of the housing of the patient module, it is guaranteed that moisture carried along by exhaled breathing gas cannot penetrate such a tube and thus cannot impair the fluidic conductivity thereof. An arrangement of a sensor mechanism spaced apart from the patient module has, in addition, the advantage that the sensor mechanism can be reused after the use thereof for ventilating a patient together with a different patient module. The same applies to an arrangement of a valve drive or of a plurality of valve drives spaced apart from the patient module for the valve or each valve comprised by the valve section. Such valve drives may also possibly be reused. In addition, a tube connection (tube connection for pressure control) between a valve drive and the components of a corresponding valve, which components are comprised by the valve section, cannot come into contact with the moisture carried along by the exhaled breathing gas, which is alone guaranteed by each valve comprised by the patient module belonging to the valve section and thus being located in the dry area of the housing. The HME filter also acts as a barrier for any microorganisms or the like carried along by the exhaled breathing gas. Thus, these microorganisms or the like also do not reach the dry area in the interior of the housing of the patient module. Thus, a basic reusability, for example, of the valve section and/or of a sensor mechanism located in the housing of the patient module and/or valve drives located in the housing of the patient module is guaranteed.

Flow is possible bidirectionally through both the valve section and the HME filter in the described sequence of the HME filter and the valve section in the interior of the patient module. In regard to the HME filter, the advantage is associated therewith that moisture carried along by the exhaled breathing gas and stored by the HME filter during breathing in, i.e., during inhalation, is discharged again to the breathing gas flowing through the patient module and the HME filter in the interior of the patient module and the patient is consequently supplied with "moistened" breathing gas.

It is noted that the patient module proposed here may also be perfected corresponding to the process claims and vice versa. Perfection of the patient module corresponding to process claims is characterized, for example, in that the patient module comprises means for executing a respective process step or the respective process steps.

In one embodiment of the patient module, this patient module comprises a particle filter between the HME filter and the valve section or behind (upstream in relation to an inspiratory volume flow) the valve section and/or the HME filter. No reference to a volume flow is, in principle, necessary in case of the position specification "between." When the position of the particle filter is nevertheless defined with reference to the expiratory volume flow, then the particle filter is located upstream of the valve section and downstream of the HME filter in relation to this volume flow. Because of this position of the particle filter, it is guaranteed that this particle filter does not come into contact with the moisture carried along by the exhaled breathing gas because this moisture is absorbed by the HME filter beforehand. The particle filter thus remains dry and at least does not change its pneumatic properties because of moisture otherwise reaching the particle filter. In addition, any microorganisms or the like carried along by the exhaled breathing gas also do not reach the particle filter. In case of the arrangement of the particle filter "behind" the valve section, provisions may concretely be made that the particle filter is in contact with the flow of the breathing gas only during inhalation (i.e., when breathing in), but not during exhalation. The resistance may thus be markedly reduced during exhalation. The valve section may correspondingly be arranged between the HME filter and the particle filter and may especially have at least one exhalation valve, but no inhalation valve. Nevertheless, in order to filter out particles from the breathing gas during the inhalation, a valve assembly may be provided, which is located upstream of the particle filter in relation to the inspiratory volume flow. The valve assembly may have an inhalation valve.

In other words, provisions may be made for the valve section (with the at least one exhalation valve) to be arranged between the HME filter and the particle filter, and the particle filter to be arranged between the valve section and a valve assembly (with the at least one inhalation valve). It is thus possible to obtain the advantage that the particle filter is only used for the inspiratory volume flow.

The HME filter described within the framework of the present invention may also be designated as a ventilation filter, especially as a Heat and Moisture Exchanger. The HME filter may be used for heat and moisture exchange, and especially as moisture and heat buffer.

The arrangement of the HME filter in relation to the expiratory volume flow upstream of the valve section may have the advantage that the valve section is located in a dry area. In other words, the HME filter carries out a filtering of the exhaled breathing gas, which, after being filtered, reaches the valve section. The arrangement thus guarantees that the expiratory volume flow and thus the breathing gas exhaled by the patient within the patient module reaches the HME filter first and the valve section only after that. If moisture is retained by the HME filter in this case, the breathing gas reaching the valve section may thus be designated as "dry."

The arrangement may possibly also be described as follows: The HME filter is located upstream of the valve section in relation to the expiratory volume flow by the HME filter and the valve section being arranged in series. This is specifically understood to mean that the HME filter and the valve section are located behind one another in a common flow duct such that a flow of the breathing gas through the HME filter and the valve section in series, i.e., behind one another, is exclusively possible. However, a parallel flow through the HME filter and the valve section, i.e., the formation of parallel flow ducts, can be ruled out. The parallel flow is prevented, e.g., by the arrangement of the HME filter and of the valve section behind one another in the common flow duct, in which no bypass or the like is provided.

The use of a particle filter in case of a patient module according to the present invention may offer another advantage. This particle filter may be used as a filter function for retaining particles and microorganisms. For this purpose, the particle filter may comprise a nonwoven material. This nonwoven material offers filter properties such as retention capacity, deep breathing resistance and a lower sensitivity to moisture in a good ratio. However, the use of the particle filter may also be associated with an increase in the construction volume to achieve a lower exhalation resistance.

Since a possible low dead space volume is needed for a ventilation, special actions may be provided for reducing the construction volume. Dead space volume is defined as the volume in the gas supply line to the patient, which volume is not exchanged in the supply line during the cyclical alternation of inhalation and exhalation. In order to avoid an enrichment of carbon dioxide in the cycle of inhalation and exhalation during the ventilation, the dead space volume must be negligibly small compared to the volume in the lungs. In particular, the HME filter and/or the particle filter and/or the valve section may be arranged geometrically such that the construction volume is overall reduced.

Therefore, provisions may be made in a patient module for at least one particle filter or precisely one particle filter to be provided, which is (respectively) configured in the form of a filter assembly, and thus has (respectively) at least two filter segments. Specifically, the particle filter—in the form of the filter assembly—may be arranged between the HME filter and the valve section. The valve section may, as an alternative, be arranged between the HME filter and the particle filter, and in particular, the particle filter in relation to an inspiratory volume flow upstream of the valve section and/or of the HME filter. In particular, the valve section may have at least one exhalation valve, and an additional valve assembly (upstream of the particle filter in relation to an inspiratory volume flow) may have at least one inhalation valve. The filter assembly may have the at least two filter segments in order to be able to make the construction volume more flexible. A flexible positioning of the filter segments in the patient module may thus take place in this manner in order to reduce the construction volume and yet to reliably provide the particle filter due to the filter segments. At least three or at most three or at least four or at most four or at most 10 filter segments may optionally be provided.

The particle filter may be configured for the flow of breathing gas through it from both sides in order to hereby make possible, e.g., a bidirectional volume flow measurement by means of the pressure drop at the particle filter and/or in order to carry out the filtering both during inhalation and during exhalation. E.g., at least one pressure sensor may be used for measuring the volume flow in order to determine the pressure drop over the particle filter. The pressure drop over the particle filter, which can be determined by means of pressure sensors and is determined during the operation of the patient module, may be used here as an indicator of the volume flow through the particle filter and thus as an indicator of a volume flow through the patient module itself and towards the patient as well.

Provisions may further be made for the filter segments to have each a filter surface (partial filter surface) in contact with the flow (especially with the expiratory volume flow and/or an inspiratory volume flow), which filter surfaces together form an overall surface (overall filter surface) of the particle filter in contact with the flow. The filter segments may be arranged and/or aligned here for parallel flow through the filter surfaces (i.e., the partial filter surfaces, especially by the respective volume flow). In particular, the volume flow or the breathing gas may thus not flow through the filter segments behind one another, but only parallel to one another. In other words, a plurality of parallel flow ducts are formed for the volume flow, in which flow ducts one of the filter segments is each located. Filter surfaces in contact with the flow, i.e., the partial filter surfaces, are defined as filter surfaces that may be in contact with the flow as well.

The use of a plurality of (i.e., at least two) filter segments of a particle filter may have the advantage that these filter segments may be used as filters, through which parallel flow is possible, each for the filtering of particles of a partial flow of the overall volume flow. Hence, only a part of the entire breathing gas flows parallel through the respective filter segments during the inhalation and/or the exhalation. The filter segments may preferably be arranged here such that the overall surface active for filtering and/or flow through the particle filter (overall filter surface) is formed by the partial filter surfaces of the filter segments (e.g., as a sum of the partial filter surfaces). In this case, the arrangement may also take place such that this overall filter surface is enlarged as much as possible towards a particle filter, which does not have a plurality of filter segments. Especially when using nonwovens for the filtering of particles, the surface rather than the volume may be essential in order to achieve a pressure loss that is as low as possible with sufficient filtering (i.e., especially retaining capacity).

The pressure loss can thus be reduced by enlarging the overall filter surface of the particle filter. In this case, the many-sided geometric design freedom during the use of a plurality of filter segments may provide the advantage that the construction volume and thus the dead space volume are not excessively enlarged or even reduced in spite of enlarging the surface.

Especially a convoluted arrangement of the filter segments may further be expedient in order to obtain a large overall filter surface with reduced construction volume.

An overall filter surface may be, e.g., in the range of 500 mm2 to 5,000 mm2, especially in the range of 1,000 mm2 to 3,000 mm2, and preferably in the range of 1,500 mm2 to 2,500 mm2. A partial filter surface may have a surface that corresponds to the overall filter surface divided by the number of the filter segments. A diameter of the respective filter segments is, e.g., in the range of 5 mm to 50 mm, especially 15 mm to 35 mm, and preferably 20 mm to 30 mm.

Provisions may further be made within the framework of the present invention for the filter segments to be arranged spaced apart from one another (especially with a space between the filter segments), so that at least one flow space is formed between the filter segments in order to flow parallel through the filter surfaces (i.e., the partial filter surfaces of the filter segments that are in contact with the flow).

The space between the filter segments is, e.g., in the range of 1 mm to 10 mm, especially 2 mm to 8 mm, and preferably 3 mm to 5 mm. In this case, the space between the filter segments may be the maximum distance between two filter segments located closest to one another. Separating devices, which are configured, e.g., as a wall or the like, may be provided between the filter segments located closest to one another. The separating devices are thus arranged in the free space between the filter segments, which free space is caused by the space, and may, e.g., cut these filter segments in half. The flow space, which has a respective volume, which essentially corresponds to the half volume of the free space, may be formed in this manner between the filter elements.

The thickness of the respective filter segment is, e.g., in the range of 1 mm to 6 mm, especially 2 mm to 4 mm. The flow spaces may each advantageously form a flow duct for the volume flow, the flow ducts being arranged parallel to one another. Other than an arrangement in series, e.g., the valve section to the HME filter and/or the HME filter to the particle filter, a parallel arrangement of the filter segments to one another in relation to the volume flow is provided here as well.

It is further conceivable that at least one separating device is provided in order to separate facing filter surfaces (i.e., the partial filter surfaces of the filter segments that are in contact with the flow) from one another in a fluid-tight manner, so that at least two flow spaces separated from one another are preferably formed between the facing filter surfaces in order to provide a parallel flow. The separated flow spaces may thus form flow ducts in the above-mentioned sense. The separating devices may be configured, e.g., as a wall or a seal or the like.

It is further possible within the framework of the present invention that the filter segments are arranged behind one another and/or are aligned bent at an angle in relation to a flow direction of the volume flow. In this connection, "behind one another" refers especially to the flow direction of the expiratory volume flow, but only to the geometric direction and not to the flow sequence of the volume flow. The flow of the volume flow may, by contrast, be parallel, which can be achieved by parallel flow spaces. This can thus be defined as a geometric arrangement in series and parallel arrangement of the filter segments in relation to the volume flow and the flow, respectively. The construction volume can thus be markedly reduced.

An arrangement of the filter segments bent at an angle is conceivable, e.g., with a respective angle in the range of 5° to 45°, especially 10° to 35° and preferably essentially 30°. A plane at right angles to the flow direction of the volume flow can be assumed as a reference for this angle. The flow direction may be defined such that a linear running through the centers of the filter segments is parallel to the flow direction, or, as an alternative, such that the flow direction corresponds to the direction, in which the housing of the patient module or the particle filter has the greatest extension (length).

The filter segments may further have at least partially a different alignment bent at an angle, and thus especially deviate from a geometrically parallel alignment. As an alternative or in addition, it is possible that the filter segments have at least partially the same alignment bent at an angle, so that filter surfaces of the filter segments are arranged (geometrically) parallel to one another.

Moreover, the valve section may optionally have at least one exhalation valve, which has the same alignment bent at an angle as at least one of the filter segments bent at an angle, preferably the filter segment located closest to the exhalation valve. The construction volume is thus further optimized.

It is further conceivable that the HME filter has a surface in contact with the flow, which surface is configured as parallel to the filter surface of at least one of the filter segments bent at an angle, preferably of the filter segment located closest to the HME filter. The construction volume for the ventilation thus also has an optimized configuration.

The filter segments may be configured as being separated in space from one another. This has the advantage that the overall filter surface and thus the resistance for the volume flow can be reduced by the simultaneous flow through the partial filter surfaces being possible.

Provisions are made in one embodiment of a patient module comprising a particle filter for the particle filter to be used as flow resistance for a pressure difference measurement, in particular for a measurement for a pressure drop over the particle filter. A special additional flow resistance is then not needed.

In this embodiment of the patient module, a measured pressure value (first measured pressure value and second measured pressure value) can be picked up each by means of two pressure sensors (first pressure sensor and second pressure sensor) to obtain a pressure difference as a result of the usual determination of a difference between the two measured pressure values, the pressure sensors being located in the interior of the patient module in relation to a gas flow through the particle filter in front of and behind the particle filter or are coupled to an area in front of and behind the particle filter. Such a coupling may be implemented, for example, by a "clip-on" or "clamp-on" device, which accommodates the pressure difference sensor and the pressure sensors, preferably including a necessary operating electronic unit and makes the pneumatic/fluidic coupling with the housing of the patient module possible. The pressure difference sensor and the pressure sensors may also be arranged in the interior of the patient module, wherein the necessary operating electronic unit may preferably be embodied in the "clip-on" or "clamp-on" device of the type mentioned above in order to make possible an electrical connection of the signals of the pressure difference sensor and of the pressure sensors to the control module. Detailed structural configurations of "clip-on" or "clamp-on" devices of the type mentioned above are not the subject of the present invention. The pressure sensors are located in the interior of the housing of the patient module in front of and behind the particle filter if the patient module itself comprises the pressure sensors. In case of pressure sensors arranged spaced apart from the patient module and located, for example, in a control module, these pressure sensors are fluidically coupled to an area in front of and behind the particle filter, for example, each by means of tubes (tube connection for pressure measurement) in front of and behind the particle filter. The relative location indication "in front of" and "behind" refers to the direction of a flow through the patient module and through the particle filter.

The use of the particle filter as flow resistance for the pressure difference measurement makes it possible to dispense with a separate flow resistance and thus avoids gas swirling within the housing of the patient module because of an otherwise necessary separate flow resistance.

In a process for the operation of such a patient module, a measured pressure value, in particular, a measured pressure value in front of the particle filter, on the one hand, and a measured pressure value behind the particle filter, on the other hand, is picked up by means of the two pressure sensors, and the pressure difference, i.e., the pressure drop over the particle filter, is determined by determining the difference between the two measured pressure values.

The pressure drop over the particle filter that can be determined by means of the pressure sensors and is determined during the operation of the patient module is an indicator of a volume flow through the particle filter and thus also an indicator of a volume flow through the patient module itself and towards the patient. The volume flow that can thus be determined can be used for a control and/or adjustment of the ventilation of the patient in a manner that is, in principle, known.

The pressure drop over the particle filter is, however, dependent on a flow resistance of the particle filter that is production-related and can hardly be accurately foreseen, as well as on a changing flow resistance of the particle filter, which can be expected during the use of the patient module. In an advantageous, special embodiment of the innovation proposed here, a calibration is correspondingly provided, which takes into account the respective flow resistance and allows a determination of the volume flow on the basis of the pressure drop over the particle filter, which determination is adapted to the respective conditions. Provisions are preferably made to the extent that a correction factor can be determined to obtain a calibrated volume flow value by means of a test volume that can be connected to the patient module or by means of a calibration resistor to a pressure drop over the particle filter, which pressure drop can be determined by means of the first pressure sensor and the second pressure sensor, the calibration resistor being able to be connected to the patient module.

In case of a process for the operation of a patient module of the type described here and below that comprises a determination of such a correction factor, a pressure drop over the particle filter, which can be determined by means of the first pressure sensor and the second pressure sensor, on the one hand, as well as a correction factor, on the other hand, are determined in case of a test volume or a calibration resistor connected to the patient module, wherein a pressure drop over the particle filter, which can be determined by means of the first pressure sensor and the second pressure sensor and a pressure drop determined by means of the first pressure sensor and the second pressure sensor during the operation of the patient module to obtain a calibrated volume flow value are weighted with the correction factor.

When the correction factor is determined by using a calibration resistor connected to the patient module, in particular a calibration resistor, to which belongs a fixed and known characteristic in relation to an input pressure acting on the calibration resistor and to a volume flow through the calibration resistor, the calibration comprises the following steps: A pressure drop over the particle filter is determined by means of the first pressure sensor and the second pressure sensor at a ventilation pressure that is predefined and is acting on the patient module. A volume flow through the calibration resistor belongs to the determined ventilation pressure because of the characteristic of the calibration resistor. The correction factor is determined on the basis of this volume flow.

When the correction factor is determined using an inflatable bag with a known bag volume, which bag is connected to the patient module and acts as a test volume, the calibration comprises the following steps: A ventilation pressure is applied to the patient module and the volume of the bag is filled under the action of the ventilation pressure. During the filling of the bag or after the filling of the bag, an area under a curve of a pressure drop over the particle filter, which curve is determined by means of the first pressure sensor and the second pressure sensor, is determined as an indicator of a volume of the bag (measured and numerically determined bag volume). Finally, the correction factor is determined on the basis of the ratio of the known bag volume to the measured volume of the bag.

In a special embodiment of such an operating process, an inverse volume flow, which is expected following the filling of the bag, is monitored for checking and for the automatic qualification of a determined correction factor as valid or invalid. If such an inverse volume flow cannot be seen or cannot be seen to a sufficient extent, the correction factor is discarded.

The process being described here and below for the operation of the patient module is embodied for the automated execution preferably in the form of a computer program. Thus, the present invention is, on the one hand, also a computer program with program code instructions that can be executed by a processing unit in the form of or like a microprocessor and a storage medium comprising such a computer program, on the other hand, i.e., a computer program product with program code means (especially commands), as well as finally also a patient module with such a processing unit and with a memory, which patient module is provided for use during ventilation of a patient and in which such a computer program is loaded or can be loaded for executing the process and its embodiments.

When process steps or sequences of process steps are being described here and below, this refers to actions, in case of an implementation of the process in software, which actions are taken because of the computer program or under the control of the computer program, provided that reference is not expressly made that some actions are brought about by a user of the computer program. Each use of the term "in an automated manner" at least means that the action in question is taken because of the computer program or under the control of the computer program.

Instead of a computer program with individual program code instructions, the process described here and below may also be implemented in the form of firmware. It is clear to the person skilled in the art that an implementation in firmware or in firmware and software or in firmware and hardware is also always possible instead of an implementation of a process in software. The fact that other implementation possibilities, specifically especially an implementation in firmware or in firmware and software or in firmware and hardware, are also covered by the term software or by the terms control program and computer program shall therefore apply to the specification being submitted here.

Exemplary embodiments of the present invention will be explained in more detail below based on the drawings. Subjects or components corresponding to one another are provided with the same reference numbers in all figures.

The exemplary embodiment or each exemplary embodiment is not understood to be a limitation of the present invention. Rather, variants and modifications are possible within the framework of the present disclosure, especially such variants and combinations, which become apparent to the person skilled in the art with regard to accomplishing the object by combining or modifying individual features described in conjunction with the features described in the general or special section of the description as well as features contained in the claims and/or in the drawings and lead to a new subject due to combinable features.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1A:
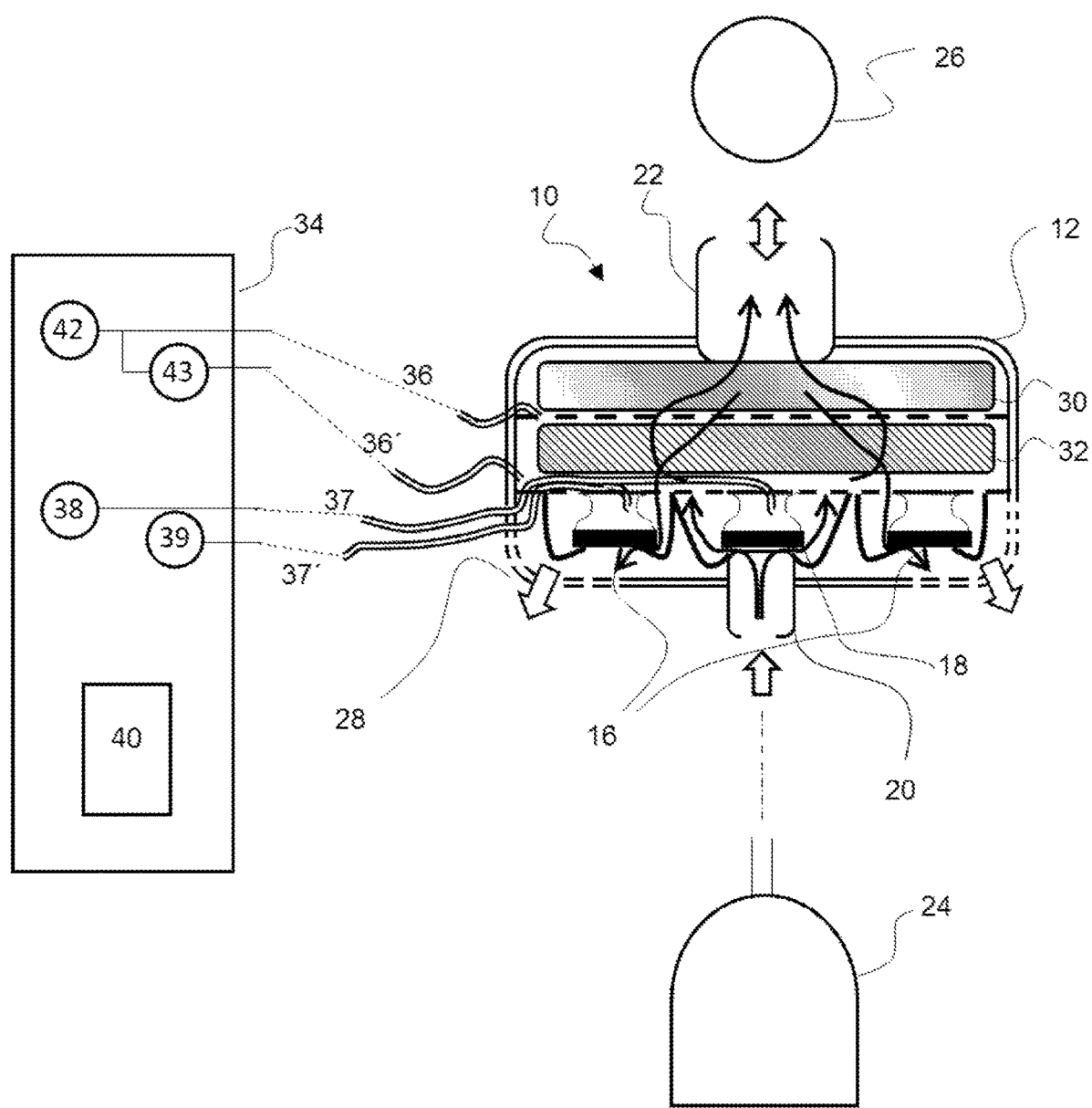
FIG. 1a is a schematic view showing an embodiment of a patient module.

Referring to the drawings, the views in FIGS. 1a through 1e show individual embodiments of the device for ventilating a patient being proposed here as examples. Such a device is designated here and below as a patient module 10. The patient module 10 comprises a housing 12 and a valve section 14 (a section with at least one valve 16, 18) in the interior of the housing. The patient module 10 is shown in each case in a sectional view, so that the view of the interior of the housing 12 is free. The valve section 14 comprises at least one exhalation valve 16. In the embodiments being shown, the patient module 10 comprises two or more exhalation valves 16, and precisely two exhalation valves 16 can be seen in the viewing direction selected for the views in FIGS. 1a through 1e. In addition to the at least one exhalation valve 16, the patient module 10 comprises an (in principle, optional) inhalation valve 18 in the embodiments shown. The view of the valves 16, 18 is highly simplified. Reference is made to the older application 10 2017 009 603 mentioned in the introduction for additional details. Basically only the movable closing elements and an elastic and to some extent collar-like membrane carrying the closing element and adjoining the closing element at the edge can be seen in the drawings in FIGS. 1*a* through 1*e*.

The patient module 10 has a coupling element 20 on the input side as connection on the input side and a coupling element 22 on the output side as connection on the output side. The patient module 10 can be coupled to a pressure source 24 by means of the coupling element 20 on the input side in an, in principle, known manner. For example, a pressurized gas cylinder acts as pressure source 24. As an alternative, a conventional ventilator of the type mentioned in the introduction also comes into consideration, in principle, as a pressure source 24. By means of the coupling element on the output side 22, the patient module 10 can be coupled to a patient interface 26, for example, a face mask in a manner that is likewise, in principle, known. The coupling element on the output side 22 acts accordingly as a patient access and can correspondingly also be designated as a patient access. A so-called medical cone, for example, comes into consideration as a coupling element 20, 22. The patient module 10 fluidically couples the pressure source 24 to the patient interface 26, which can be connected to the airways of a patient and which is connected to the airways of a patient during the ventilation. The patient module 10 can be detachably connected to the patient interface 26 and to the pressure source 24 by means of the two coupling elements 20, 22.

The patient module 10 is intended for use close to the patient (close to the patient). In this respect, the patient module 10 may be connected, for example, directly to the patient interface 26 or by means of a comparatively short piece of tube to the patient interface 26. The length of such a piece of tube should not exceed 10 cm.

The coupling element 20 on the input side and/or the coupling element on the output side 22 are optionally located—as shown by way of example—in the center of a respective surface section of the housing 12 of the patient module 10, especially in the center of a planar or essentially planar surface section of the housing 12 of the patient module 10. The inhalation valve 18 directly or indirectly adjoins the coupling element on the input side 20 (embodiments according to FIGS. 1*a* through 1*d*). In case of a central arrangement of the inhalation valve 18 and a patient module 10 with a plurality of exhalation valves 16, these valves are optionally distributed uniformly spaced apart about the central inhalation valve 18, for example, along a circular line.

In the views in FIGS. 1*a* through 1*d*, the block arrow pointing in the direction of the interior of the patient module 10 represents, on the one hand, a pressure present at this patient module when the inhalation valve 18 is closed because of a corresponding pressure source 24 and, on the other hand, a volume flow reaching the patient module 10 during an inhalation from the pressure source 24. The volume flow reaching the patient module 10 during inhalation is intended for ventilating the patient and is correspondingly discharged on the output side via the coupling element on the output side 22 in the direction of the connected patient interface 26 and thus in the direction of the patient. During exhalation, the patient exhales via the patient interface 26 and the patient module 10. The double-ended block arrow in the area of the coupling element on the output side 22 represents, on the one hand, the volume flow towards the patient, especially during inhalation, and, on the other hand, the volume flow away from the patient, especially during exhalation. Breathing gas exhaled by the patient during exhalation flows through the housing 12 of the patient module 10 and leaves same through at least one housing opening 28 provided for this. An embodiment with a plurality of housing openings 28 is shown in the views in FIGS. 1*a* through 1*e*, and the block arrows pointing outwards from the interior of the housing 12 illustrate a volume flow, resulting during the exhalation of the patient, from the interior of the housing 12 into the surrounding area.

The described volume flows during inhalation and during exhalation enter the interior of the patient module 10 through a so-called HME filter 30 as well as through a particle filter 32. The HME filter 30 and the particle filter 32 are arranged in parallel planes and spaced apart from one another in the interior of the housing 12 of the patient module 10 and are supported there, for example, by means of a bottom (not shown) with a grid structure or by means of a plurality of such bottoms. The HME filer 30 and optionally also the particle filter 32 adjoin at the edge (in a positive-locking manner or in a press fit) the adjacent inner surface of the housing 12 or a seal or the like located there. In any case, it is guaranteed that a volume flow through the patient module 10 passes completely through the HME filter 30. The HME filter 30 is facing the coupling element on the output side 22 in the interior of the patient module 10. I.e., the HME filter 30 is located between the coupling element on the output side 22 and the particle filter 32 and an inspiratory volume flow passes through the HME filter 30 before entry into the coupling element on the output side 22 and an expiratory volume flow passes through the HME filter 30 from the coupling element on the output side 22 and before the further entry into the interior of the patient module 10. The particle filter 32 is in this sense facing the valve section 14 with the at least one exhalation valve 16 as well as the coupling element on the input side 22 and the housing opening or each housing opening 28. I.e., the particle filter 32 is located between the HME filter 30 and the valve section 14 and an inspiratory volume flow passes through the particle filter 32 before the further entry into the interior of the patient module 10 and before this flow reaches the HME filter 30. The views in FIGS. 1*a* through 1*e* show each a preferred, but, in principle, optional embodiment of the patient module 10, in which the HME filter 30 and the particle filter 32 have surfaces of equal size or of at least essentially equal size in contact with the flow and are aligned flush with one another in relation to the edges of these surfaces. In case of such a configuration, the breathing gas exhaled during exhalation also passes through the particle filter 32 and from there reaches the exhalation valve or each exhalation valve 16.

The HME filter 30 is located downstream of the particle filter 32 ("behind" the particle filter 32) in relation to a direction of the volume flow in case of inhalation (from the coupling element on the input side 20 to the coupling element on the output side 22). During exhalation, the HME filter 30 is located "in front of" the particle filter 32. When breathing out, i.e., during exhalation, breathing gas thus reaches the interior of the housing 12 of the patient module 10 first at the HME filter 30 and the moisture carried along by the breathing gas is absorbed there and retained in the HME filter 30. The interior of the housing 12 of the patient module 10 is thus "dry" downstream of the HME filter 30 (in relation to the direction of the volume flow during exhalation). The views in FIGS. 1*a* through 1*e* show in this respect a dashed line between the HME 30 and the particle filter 32, which line symbolizes a limit between a dry area in the interior of the housing 12 of the patient module 10 (particle filter 32, valve section 14, coupling element on the input side 20) and a wet area in the interior of the housing 12 of the patient module 10 (HME filter 30, coupling element on the output side 22).

During inhalation, the HME filter 30 discharges at least a portion of the previously absorbed, stored moisture again to the breathing gas finally reaching the patient. Equilibrium has been established here within a few breaths: The HME filter 30 absorbs moisture during exhalation. The HME filter 30 discharges previously absorbed moisture again to the breathing gas flowing through the HME filter 30 during inhalation. The same also applies to a quantity of heat absorbed by the HME filter 30 during exhalation. At least a portion thereof heat is also again discharged to the breathing gas finally reaching the patient during inhalation. The breathing gas reaching the patient is thus both moistened and heated by means of the HME filter 30.

The particle filter 32 is essentially intended for the protection of the patient in a manner which is, in principle, known and ensures that during inhalation no particles, foreign bodies and the like reach the patient, where they could otherwise reach the lungs of the patient.

The valve section 14, i.e., the at least one exhalation valve 16 or any number of exhalation valves and inhalation valves 16, 18 comprised by the patient module 10, is located in the interior of the patient module 10 in the dry area there. One advantage that is obtained due to this arrangement is that the valve membranes and the craters, which can be closed by means of the respective closing element, remain dry. Wet membranes tend to adhere (stick) to one another or to have a nonlinear opening characteristic. This is especially problematic at very low temperatures. The exhalation valve 16 is especially affected thereby.

The dry area in the interior of the housing 12 of the patient module 10, i.e., the area with the valve section 14 up to and including the particle filter 32, also comes into consideration as a location for a sensor mechanism for acquiring individual measured values. Optionally, such a sensor mechanism may also be entirely or partially located spaced apart from the patient module 10 in a separate part of the device, which is associated with the patient module 10 and is designated below as control module 34.

A configuration with such a spaced apart sensor mechanism is shown as an example in the view in FIG. 1a. The connection between the patient module 10 and the control module 34 is in the form of individual tubes 36, 36', 37, 37', which may optionally be combined all together or in groups while obtaining each individual ducts through which flow is possible. The tubes 36, 36', 37, 37' end in the interior of the housing 12 of the patient module 10 in the dry area there. This guarantees the possibility of flow through the ducts in the interior of the tubes 36, 36', 37, 37'. In particular, it has been shown that small or minuscule quantities of condensate, as they are to be expected in the area of the HME filter 30, may also block a tube 36, 36', 37, 37' and the tube 36, 36', 37, 37' thus has to be dried and/or flushed.

The use of tubes 36, 36', 37, 37' ending in the dry area of the patient module 10 has the advantage of an independence of the control module 34 from the patient module 10. The control module 34 as well as a sensor mechanism (a sensor device and/or sensor arrangement) located therein and/or additional functional units located therein may also be reused in case of disposal of a patient module 10 used for ventilating a patient together with a different patient module 10.

A functional unit that can be placed in the control module 34 and can thus be reused in this sense is a valve drive 38, 39 or a respective valve drive 38, 39 for each valve 16, 18 comprised by the valve section 14 or precisely one valve drive 38, 39 each, on the one hand, for all exhalation valves 16 comprised by the valve section 14 and, on the other hand, for all inhalation valves 18 comprised by the valve section 14.

Another advantage of the dry area in the interior of the housing 12 of the patient module 10 is thus that piezo pumps (micropumps), which are themselves located outside of the housing 12, especially in the control module 34, and act as valve drive 38, 39, can be connected by means of tubes 37, 37' ending there—especially in the valve section 14.

Each exhalation valve or inhalation valve 16, 18 is a valve assembly that is possibly distributed in space. On the one hand, the closing elements shown in FIGS. 1a through 1e and the membranes carrying a closing element, which are respectively also shown in FIGS. 1a through 1e, as well as, on the other hand, a valve drive 38, 39 belong to the valve assembly. The possibility of a separation in space of a valve drive 38, 39 from the remaining parts of the valve assembly has already been explained in detail in the above-mentioned older application 10 2017 009 603 (see, for example, the view in FIG. 6 there), so that reference is made to the entire description of the older application, and especially the explanations concerning FIG. 6 there, to avoid repetitions, and these shall be considered to be included in the description being submitted here.

The control module 34 preferably comes into consideration as a location for a control unit 40 for controlling and/or monitoring the patient module 10. The control unit 40 comprises in a manner that is, in principle, known a processing unit in the form of or like a microprocessor as well as a memory, into which a control program is loaded, which is executed by means of the processing unit of the control unit 40 during the operation of the patient module 10. The control module 34 thus determines the status of the valves 16, 18 of the valve section (open, closed, partly open, partly closed) as well as the times of a possible change in status under the control of the control unit 40.

The pickup of measured values is necessary for an automated determination of such times. In this respect, two pressure sensors 42, 43 are shown in the view in FIG. 1a as examples for the already above-mentioned sensor mechanism comprised by the control module 34. A measured value in relation to a pressure in the interior of the housing 12 of the patient module 10 can be picked up by means of a single pressure sensor 42, 43. Two such measured values and a pressure difference in the form of a difference of these measured values can be picked up by means of two pressure sensors 42, 43.

The pressure drop $\Delta p$ over the particle filter 32 is considered to be the pressure difference to acquire the volume flow, which is designated as volumetric flow rate and sometimes briefly as flow in the technical terminology, i.e., for flow measurement, based on a pressure difference measurement. For this purpose, the sensor mechanism comprises, for example, a first pressure sensor 32 and a second pressure sensor 43 (embodiments according to FIG. 1a and FIG. 1b). An embodiment with a sensor mechanism 42, 43 spaced part from the patient module 10 is shown in the view in FIG. 1a. The sensor mechanism 42, 43 is located in the control module 34 here. An embodiment with a sensor mechanism 42, 43 associated in space with the patient module 10 is shown in the view in FIG. 1b. In case of a sensor mechanism 42, 43 associated in space with the patient module 10, the sensors (first pressure sensor 42, second pressure sensor 43) are located in the patient module 10, i.e., in the interior of the patient module 10, or at the patient module 10, for example, outside on the housing 12 of the patient module 10.

In a sensor mechanism 42, 43 spaced apart from the patient module 10, this sensor mechanism is coupled in the interior of the patient module 10 to an area in front of and behind the particle filter 32 ("in front of" and "behind" refer each to the direction of flow through the patient module) by means of tubes 36, 36' (tubes/tube connection for pressure measurement) starting from the respective pressure sensor 42, 43 and ending in the interior of the patient module 10. The same applies to a sensor mechanism 42, 43 located at the patient module 10. In a sensor mechanism 42, 43 located in the patient module 10, the first pressure sensor 42 and the second pressure sensor 43 are located each in an area in front of and behind the particle filter 32. The end points of such tubes 36, 36' in the interior of the patient module 10 are individually designated as pressure-measuring port and together as pressure-measuring ports. A pressure-measuring port is located, for example, at the HME filter 30 or at the particle filter 32, especially on the side of the HME filter 30 at the particle filter 32 (in relation to an expiratory volume flow through the patient module 10 on the upstream side of the particle filter 32). An additional pressure-measuring port is located at the valve section 14 or at the particle filter 32, especially on the side of the valve section 14 of the particle filter 32 (in relation to an expiratory volume flow through the patient module 10 on the downstream side of the particle filter 32). The pressure-measuring port and the additional pressure-measuring port are pneumatically connected to the sensor mechanism 42, 43 by means of a respective tube 36, 36' (tube 36, additional tube 36; tube connection for pressure measurement) and a pressure difference measured value, which indicates quantities of gas flowing towards the patient or away from the patient (inhaled breathing gas, exhaled breathing gas), can be acquired by means of a sensor mechanism 42, 43 acting, for example, as a pressure difference sensor. A pressure difference measured value, which indicates quantities of gas flowing towards the patient or away from the patient, can also be acquired by means of a sensor mechanism 42, 43, the pressure sensors 42, 43 of which (first pressure sensor 42, second pressure sensor 43) act as absolute pressure sensors, by determining the difference between the measured pressure values obtained by the two pressure sensors 42, 43.

A difference between the measured values that can be obtained by the two pressure sensors 42, 43 (pressure difference value) is an indicator of the pressure drop Δp over the particle filter 32. It is essential that the pressure sensors 42, 43 be located in the dry area in the interior of the housing 12 in case of a sensor mechanism 42, 43 located in the interior of the patient module 10 and the tubes 36, 36' (tubes/tube connection for pressure measurement) starting from there in the interior of the housing 12 end in the dry area thereof in case of a sensor mechanism 42, 43 located at the patient module 10 or in the control module 34.

Figure 1B:
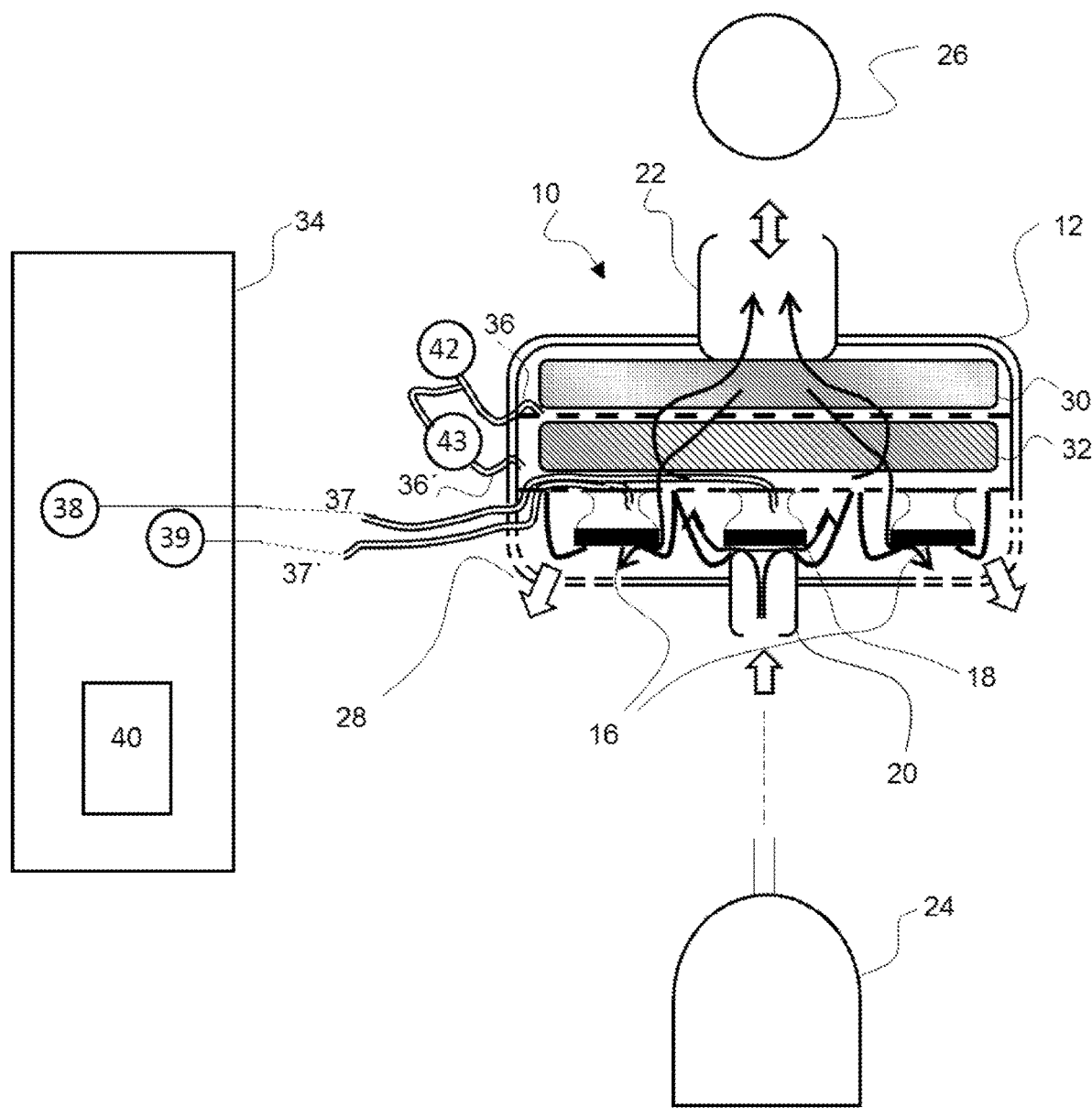
FIG. 1b is a schematic view showing a further embodiment of the patient module.
Figure 1C:
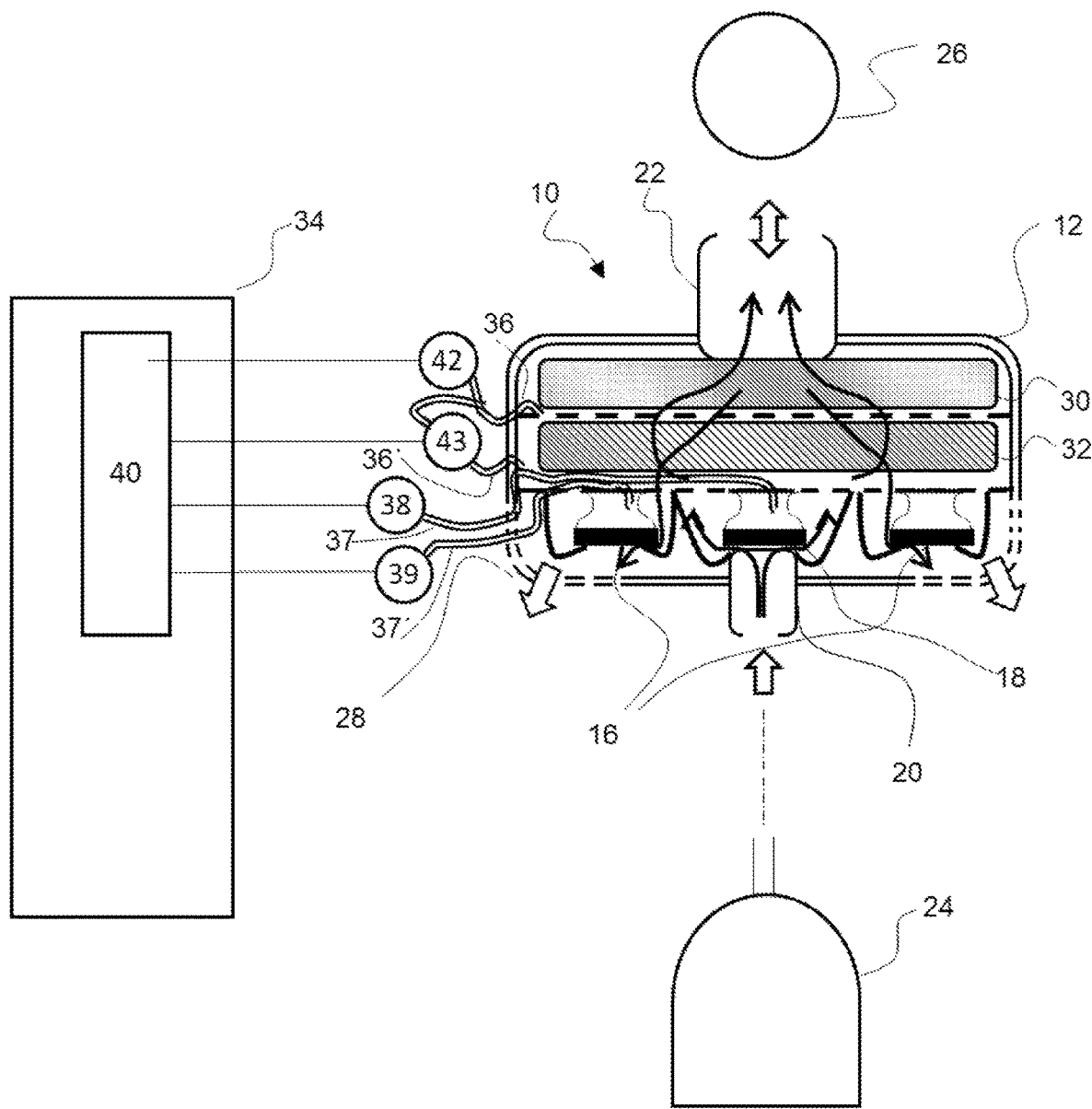
FIG. 1c is a schematic view showing a further embodiment of the patient module.
Figure 1D:
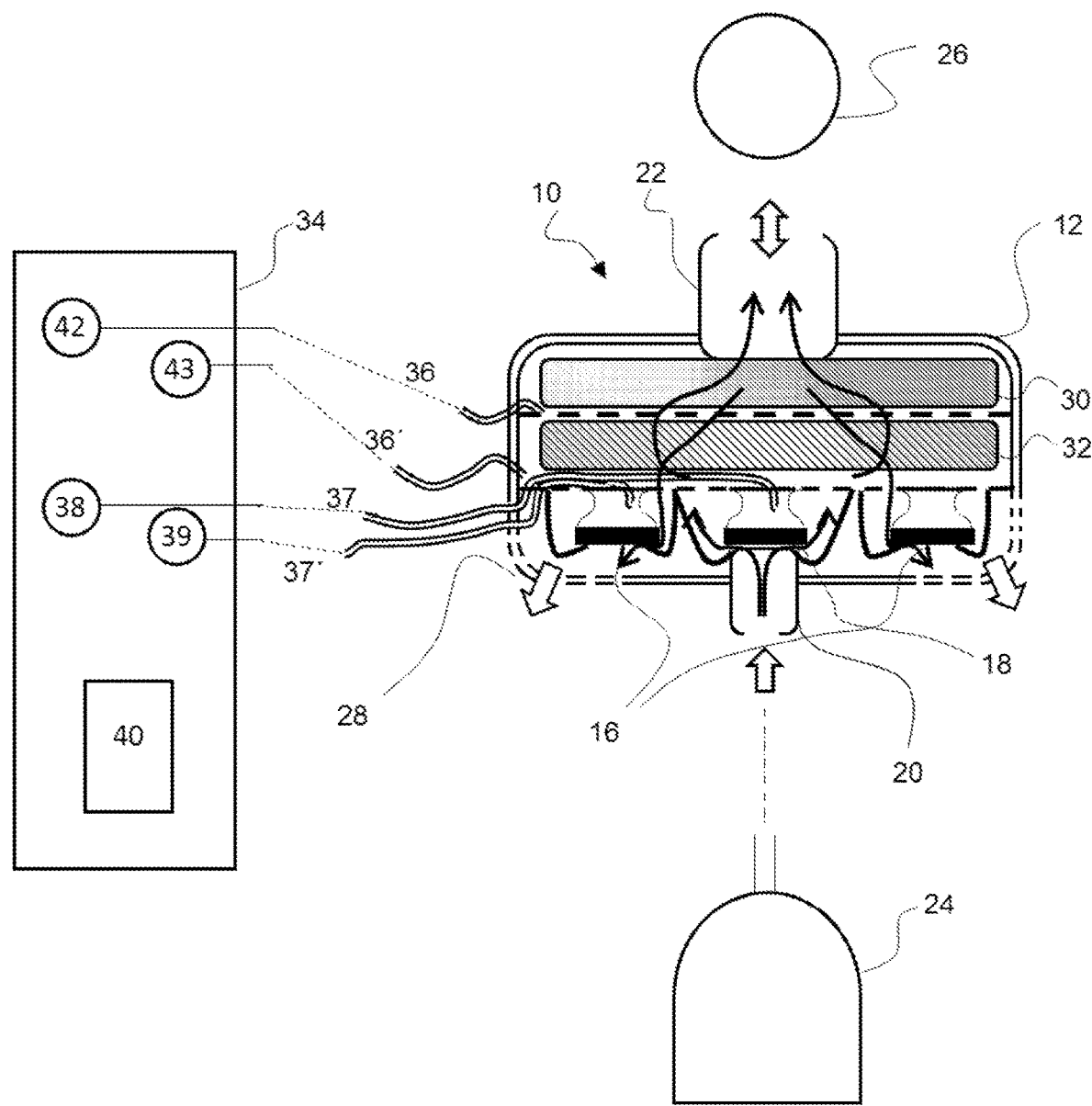
FIG. 1d is a schematic view showing a further embodiment of the patient module.
Figure 1E:
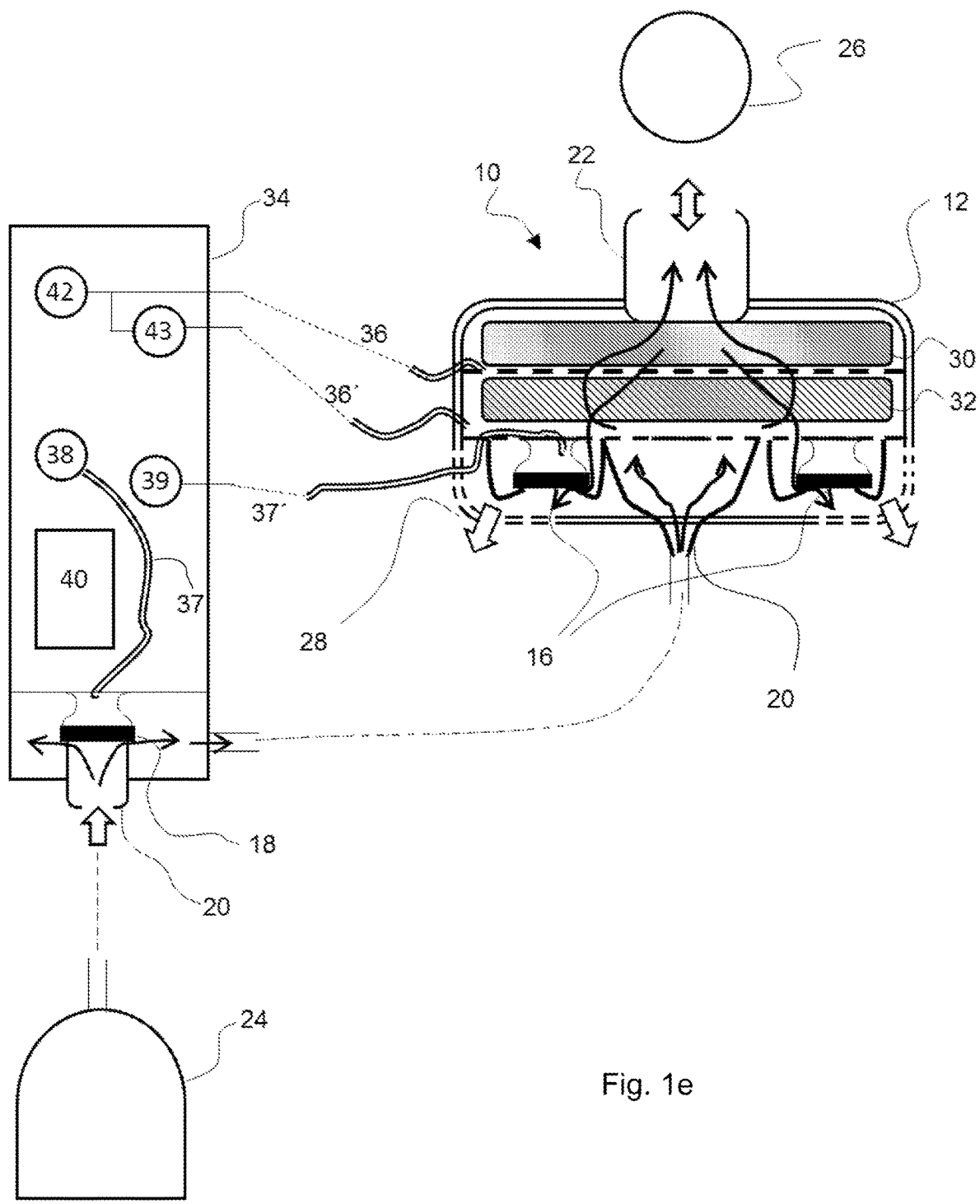
FIG. 1e is a schematic view showing a further embodiment of the patient module.

The views in FIGS. 1a through 1e show the sensor mechanism 42, 43 in the form of two pressure sensors 42, 43 (first pressure sensor 42, second pressure sensor 43), especially, on the one hand, two separate pressure sensors 42, 43, which then act each as absolute pressure sensor, or two coupled pressure sensors 42, 43, which then act together as a pressure difference sensor. In case of two separate pressure sensors 42, 43, the difference of the measured values of the two pressure sensors 42, 43 is determined to obtain a pressure difference measured value. In case of pressure sensors 42, 43 that are coupled and act together as pressure difference sensor, the pressure difference measured value is obtained directly. The views in FIGS. 1a, 1b and 1c show a coupling of the pressure sensors 42, 43 there in the form of a pneumatic connection, for example, a tube connection. The view in FIG. 1d shows two pressure sensors 42, 43 without such a connection. These pressure sensors then act correspondingly each as absolute pressure sensor. Instead of a sensor mechanism 42, 43 with two separate pressure sensors 42, 43, a sensor mechanism 42, 43 with two coupled pressure sensors 42, 43 and vice versa also always comes into consideration, so that this can always be added and read conceptually especially in any mention of the term sensor mechanism 42, 43, in addition to the embodiments shown. In case of a sensor mechanism 42, 43 in the patient module or at the patient module 10, electric energy is supplied by means of electrical lines (not shown) to the sensor mechanism 42, 43, and at least one measured value is sent from the sensor mechanism 42, 43 by means of an additional electrical line (not shown). Such lines from and to the patient module 10 are not necessary in case of a sensor mechanism 42, 43 and the energy supply and measured value transmission may take place entirely within the control module 34.

The views in FIGS. 1a, 1b and 1d show an embodiment of the patient module 10 with valve drives 38, 39 that are spaced apart from the patient module 10. The valve drives 38, 39 are located in the control module 34 in case of the embodiment shown. The view in FIG. 1c shows an embodiment with valve drives 38, 39 associated in space with the patient module 10. In case of valve drives 38, 39 associated in space with the patient module 10, these valve drives are located in the patent module, i.e., in the interior of the patient module 10, or at the patient module 10, for example, outside on the housing 12 of the patient module 10. The inhalation valve 18 is located in the control module 34 in the embodiment shown in FIG. 1e. The inhalation valve 18 is pneumatically connected to its valve drive 38 within the control module 34. The exhalation valve or each exhalation valve comprised by the valve section 14 in the patient module 10 is pneumatically (tube 37') connected to the valve drive 39 comprised by the control module 34. All variants shown can be combined with one another as desired in relation to the location of the sensor mechanism 42, 43, in relation to the location of the valve drive or each valve drive 38, 39 as well as in relation to the location of an, in principle, optional inhalation valve 18, so that the description submitted here also comprises, for example, an embodiment with an inhalation valve 18 comprised by the control module 34 (according to FIG. 1e) and with a sensor mechanism 42, 43 associated in space with the patient module 10 (according to FIGS. 1b, 1c), etc.

Because of the structure of the filter material of the particle filter 42 with very many, very small ducts, a largely laminar flow through the particle filter 32 and thus a linear relationship between the pressure difference value determined in the form of the pressure drop Δp over the particle filter 32 and the volume flow: Q=factor×Δp are obtained. The factor "factor" is uniformly fixed for the flow resistance of the particle filter 32. This factor has the value, for example, 0.3 mbar at 30 L/min.

In an embodiment with two separate pressure sensors 42, 43, a measured value picked up by means of a pressure sensor 43 (second pressure sensor 43), the tube 36' of which ends in the interior of the housing 12 of the patient module 10 in the area of an intermediate space between the valve section 14 and the particle filter 32, is an indicator of an airway pressure (pAW) of the patient.

Because of the arrangement of the particle filter 32 in the dry area of the interior of the housing 12 of the patient module 10, this particle filter also remains dry because moisture carried along by the exhaled breathing gas is absorbed by means of the HME filter 30 upstream of the particle filter 32 during exhalation. Therefore, the particle filter 32 does not change its pneumatic resistance even during the ventilation of a patient because of moisture-related effects, because the particle filter 32, for example, does not swell, as this would otherwise be expected in case of an entry of moisture.

The laminar pressure drop $\Delta p$ per volume flow is, as is generally known, dependent, on the one hand, on the dynamic viscosity of the gas medium and, on the other hand, on the temperature $\vartheta$: The laminar volume flow $Q=dV/dt$ increases linearly with the pressure drop $\Delta p$ and with the reciprocal value of the dynamic viscosity $\eta$. The dynamic viscosity $\eta$ increases linearly with the square root of the temperature $\vartheta$: $Q \sim \Delta p/\eta$; $Q \sim \Delta p/\sqrt{\vartheta}$.

The flow resistance of the particle filter 32 (flow resistance) is subject to changes over the course of time. The resistance increases due to an increasing coating of particles, whereas temperature and air humidity changes tend to result in a varying resistance value.

Figure 2:
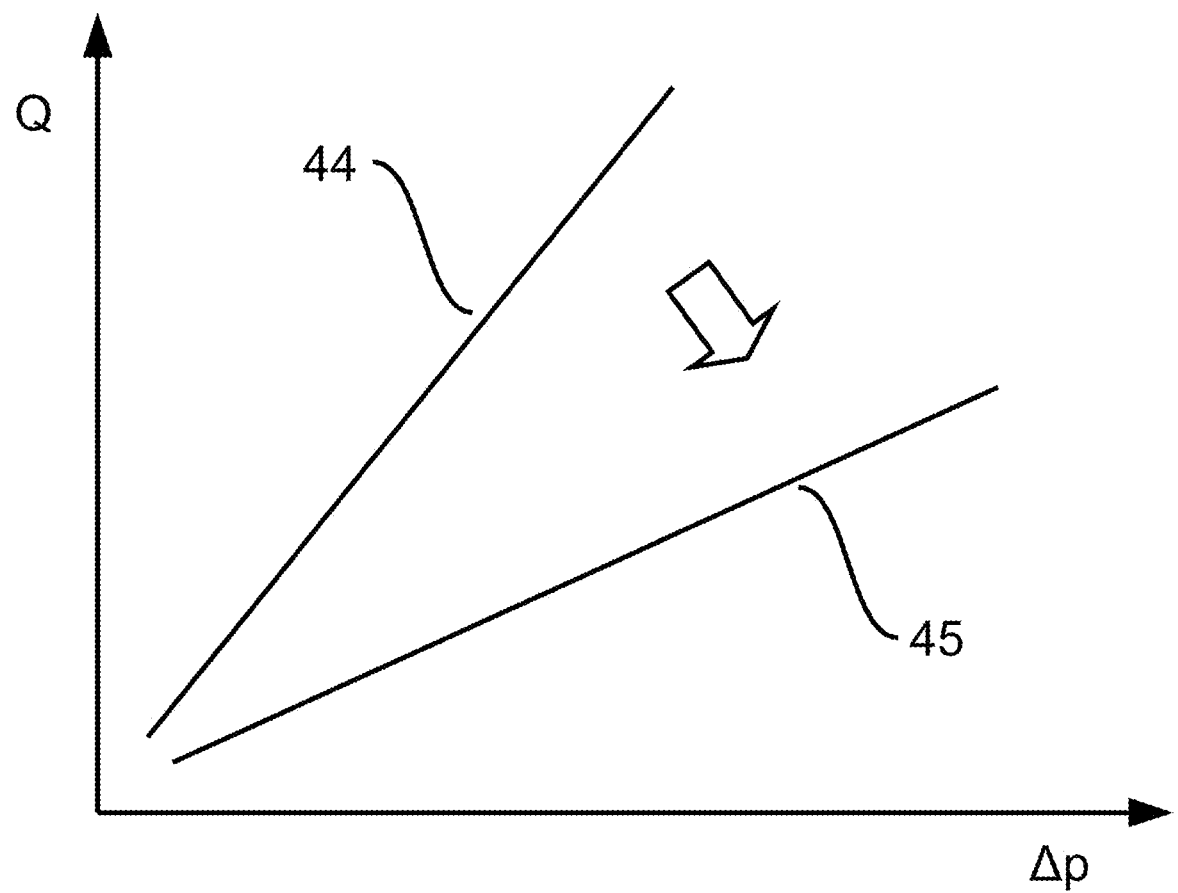
FIG. 2 is a graph showing two characteristics.

The view in FIG. 2 shows two characteristics 44, 45 for the dependence of the volume flow Q on the pressure drop $\Delta p$, the pressure drop $\Delta p$—as proposed here—being optionally determined via the particle filter 32. In this case, a first characteristic 44 shows the correlation at low temperatures ("cold") and a second characteristic 45 shows this correlation at higher temperatures ("hot"), and temperatures, for example, in the range of 0° C. to 5° C. are regarded as low temperatures and temperatures, for example, in the range of 25° C. to 30° C. are regarded as higher temperatures.

With an increase, for example, in ambient temperature, especially because of daytime or seasonal temperature fluctuations, the correlation of volume flow Q and pressure drop $\Delta p$ comes closer and closer to the second characteristic 45 as this is suggested by the block arrow pointing to the second characteristic 45.

Two particle filters 42 intended for use in different patient modules 10 are only precisely equal in exceptional cases, and different pneumatic characteristics, especially different flow resistances are obtained, for example, because of production-related different thicknesses, densities and/or a different homogeneity, etc. In case of particle filters 32 that are unequal in this respect, unequal volume flows result at equal ventilation pressure. Consequently, the correlation between the pressure difference value determined in the form of the pressure drop $\Delta p$ over the particle filter 32 and the volume flow (Q=factor×$\Delta p$) mentioned further above makes a correction meaningful, by means of which such different characteristics are taken into consideration.

In addition, a change in the flow resistance of the particle filter 32, for example, also because of an increasing coating of particles also occurs during the operation of the patient module 10. The flow resistance as the ratio of a ventilation pressure acting on the particle filter 32 to a volume flow through the particle filter 32 resulting because of the ventilation pressure becomes greater. As a result, the correlation between the pressure difference value determined in the form of the pressure drop $\Delta p$ over the particle filter 32 and the volume flow (Q=factor×$\Delta p$) mentioned further above also makes a correction meaningful if the flow resistance of the particle filter 32 changes.

Such a correction is possible and optionally provided in the patient module 10 being proposed here. The correction is designated below as calibration. The correction can be carried out after a certain duration of use of the patient module 10 or uniformly—provided the application situation allows the brief interruption of the use of the patient module 10 during the ventilation of the patient from a medical view. A calibration may also take place before beginning the use of the patient module 10 instead of such a calibration parallel to the use of the patient module 10 or in addition to or as an alternative to such a use-parallel calibration.

A calibrated value for the volume flow is necessary in cases, in which the volume flow itself, the integrated volume or other dynamic variables derived from the volume flow, as this is necessary, for example, during measurement actions to determine the so-called resistance or to determine the so-called compliance take on a special importance during the ventilation of a patient. A calibrated volume flow measured value is meaningful additionally and independently of the above statements when production tolerances of the particle filter 32 and varying filter resistances resulting therefrom shall be compensated.

Figure 3:
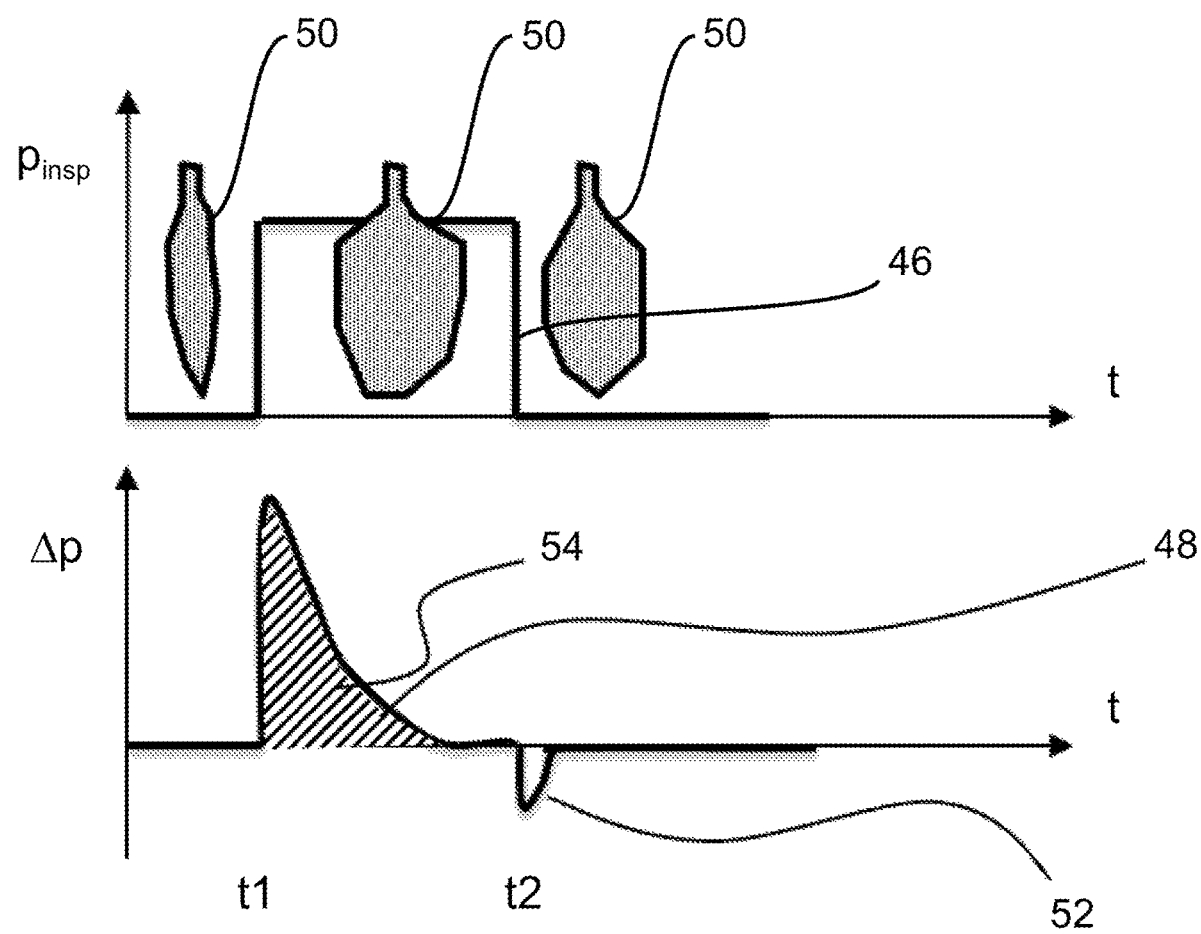
FIG. 3 is a graph showing ventilation pressure curves and resulting curves of a pressure drop in the interior of the patient module.

The calibration process is explained based on the view in FIG. 3. FIG. 3 shows a ventilation pressure curve 46 and a resulting curve of a pressure drop 48 in the interior of the patient module 10 in case of an elastic bag coupled to the patient module 10.

FIG. 3 shows, in the upper area, the curve of a ventilation pressure (inspiratory pressure) pinsp, which is discharged from the patient module 10 at the coupling element on the output side 22 thereof, over time t (ventilation pressure curve 46) and the curve of the pressure drop $\Delta p$ (pressure drop curve 48) in the interior of the patient module 10 over the same time axis in the lower area. The curve 46 of the ventilation pressure pinsp shown is obtained by the inhalation valve 18 being opened at a time t1 and consequently by the ventilation pressure pinsp acting in the interior of the patient module 10 as well as at the coupling element on the output side 22 and by the inhalation valve 18 being closed again at a later time t2 and thus the action of the ventilation pressure pinsp ending in the interior of the patient module 10. The shown curve 18 of the pressure drop $\Delta p$ over the particle filter 32 in the interior of the patient module 10 and a proportional curve of the volume flow Q are obtained by there being a large pressure drop $\Delta p$ over the particle filter 32 immediately after the opening of the inhalation valve 18 because of a now resulting initial pressure equalization, and correspondingly by a high volume flow resulting and by the pressure drop $\Delta p$ and the volume flow Q decreasing with increasing pressure equalization.

For the calibration, a bag 50, for example, acting as test volume, especially a bag 50 with a known volume Vist, is connected to the coupling element on the output side 22, i.e., for example, plugged onto the coupling element on the output side 22. The bag 50 is shown in the upper area of the view in FIG. 3. The bag 50 is brought into a defined starting state at the beginning of the calibration, i.e., for example, folded flat or pressed flat. The starting state of the bag 50 is shown on the far left side in the view in FIG. 3, i.e., for the time before the time t1. With the opening of the inhalation valve 18 at the time t1, a respective fluid flows over the inhalation valve 18 and through the patient module 10, i.e., also over the particle filter 32, into the bag 50. The bag 50 expands more and more in this case. A snapshot of a bag 50 expanding when the inhalation valve 18 is opened is shown in the center in the view in FIG. 3, i.e., for the time after the time t1 and before the time t2. The time t2 is selected such that the volume of the bag 50 is filled with breathing gas flowing through the patient module 10 into the bag 50 at least at the time t2. When the inhalation valve 18 closes at the time t2, a release of the bag 50 takes place with a fully filled and intact bag 50 and a resulting inverse volume flow 52 is shown in the lower area of the view in FIG. 3 following the time t2.

The area 54 under the measured value curve of the pressure drop Δp (the integral over the measured value curve of the pressure drop Δp) corresponds to a measured and numerically determined value Vmess for the volume of the expanded bag 50. When this value corresponds to the actual volume Vist of the expanded bag 50, no correction is needed. However, a deviation between the measured and numerically determined volume Vmess, on the one hand, and the known, actual value Vist, on the other hand, usually occurs, and to compensate for such a deviation, the pressure drop over the particle filter 32 which can be determined by means of the sensor mechanism 42, 43 is acted on (calibrated) with the ratio of the known bag volume Vist to the measured volume Vmess of the bag 50 and the volume flow is determined as follows: Q=factor×correction×Δp. The respective pneumatic characteristics and/or a changing flow resistance of the particle filter 32 are taken into consideration by means of the correction factor "correction." The latter takes place because of an increasing contamination (coating of particles) of the particle filter 32 (concisely) and the correction factor "correction" is obtained as a quotient of the actual volume Vist of the bag 50 to the measured and numerically determined value Vmess: Correction=Vist/Vmess. At the time of delivery, i.e., when the patient module 10 is delivered, the correction factor "correction" is set to the value "1.0."

A sensing of a "negative" pressure drop Δp belonging to an inverse volume flow 52 over the particle filter 32 immediately following the time t2 may optionally be used for the automatic qualification of a correction value determined as described above as valid or invalid. An inverse volume flow 52 is obtained immediately following the time t2 because of a certain elasticity of the bag 50 and in case of a bag 50 that is fully filled up to the time t2 at the latest and is intact. The inverse volume flow 52 is then the result of a release of the bag 50. Such a release is not obtained if the bag 50 is not fully filled and/or if the bag 50 is damaged. If the negative pressure drop Δp over the particle filter 32 falls short of a predefined or predefinable threshold value within a short time window of predefined or predefinable duration after the time t2, this indicates a bag 50 that is sufficiently filled beforehand and, in addition, is intact, and the correction value can be used (valid correction value). By contrast, if the threshold value is not reached, the correction value is automatically discarded (invalid correction value) and an optical and/or acoustic signal element is, for example, activated to display the failed calibration.

Figure 5:
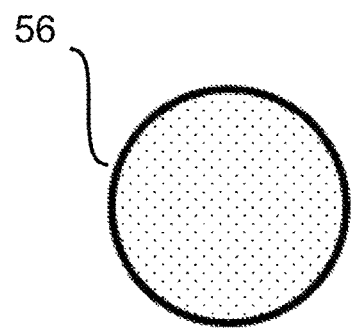
FIG. 5 is a schematic view showing a calibration resistor that can be coupled to the patient module.

A similar process for taking into consideration the pneumatic characteristics of a respective particle filter 32 and/or of a changing flow resistance of the particle filter 32 in case of the determination of a calibrated volume flow on the basis of a pressure drop Δp measured in the patient module 10 is obtained when, instead of the bag 50, a pneumatic calibration resistor 56 (FIG. 5) is mounted at the coupling element on the output side 22. This calibration resistor may be a component of a dust cover or may have a dual function as a calibration resistor 56 and as a dust cover, which is delivered with the patient module 10 or with the HME filter 30. Such a calibration resistor 56 has a fixed and known characteristic in relation to an input pressure acting on the calibration resistor 56 and a respective resulting volume flow through the calibration resistor 56. A volume flow, for example, of Qist=60 L/min is obtained if a ventilation pressure pinsp of, for example, 20 mbar is applied to the patient module 10 in case of a mounted calibration resistor 56. The measured pressure drop p over the particle filter 32 is related to this volume flow (Qist) and the correction factor "correction" is determined such that Qist=factor×correction×Δp applies. The value for the correction factor "correction" that is necessary for this is obtained with: Correction=Qist/(factor×Δp).

Figure 4:
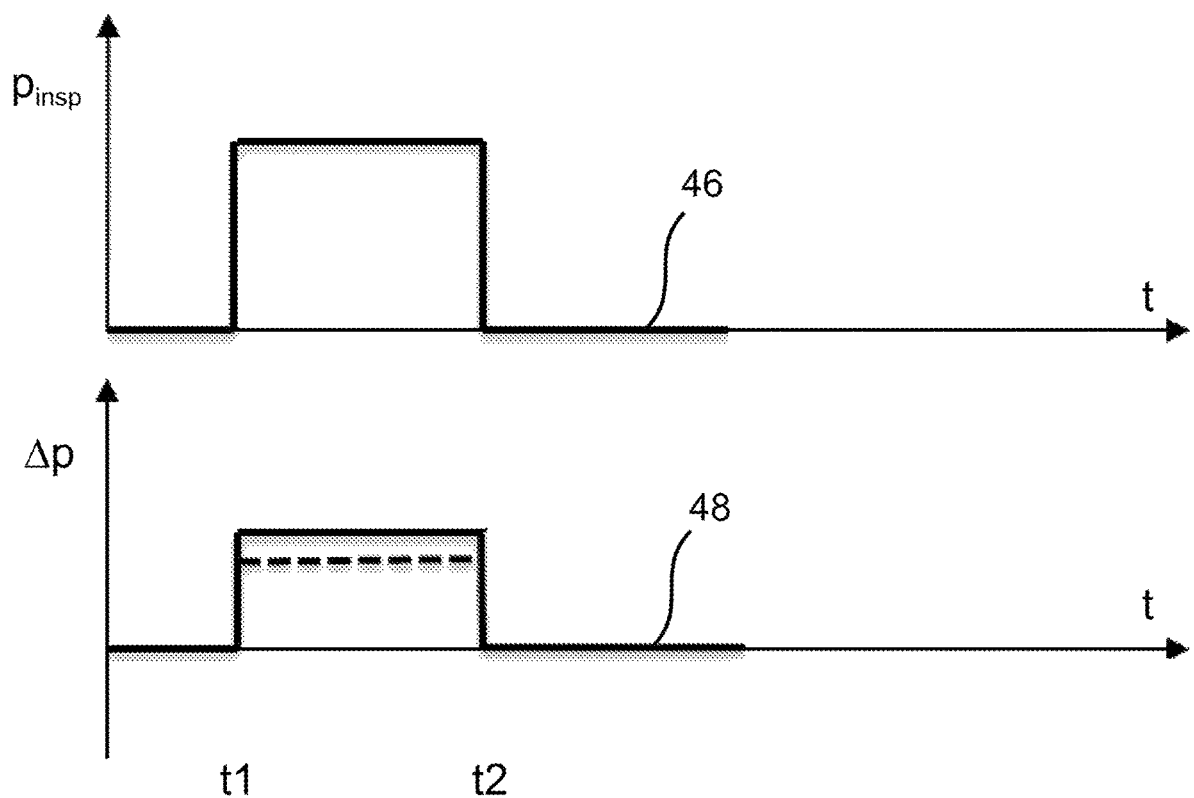
FIG. 4 is a graph showing ventilation pressure curves and resulting curves of a pressure drop in the interior of the patient module.

The view in FIG. 4 shows a curve of a ventilation pressure (ventilation pressure curve 46) applied to a patient module 10 in case of a calibration resistor 56 mounted at the patient module 10 and a resulting curve of a pressure drop Δp (pressure drop curve 48) in the interior of the patient module 10, especially over the particle filter 32. In case of the pressure drop curve 48 shown, the solid line represents the measured conditions and the dashed line represents expected conditions, especially conditions expected because of the mounted calibration resistor 56.

A cover which can be placed onto the coupling element on the output side 22 acts as the calibration resistor 56. The cover has optionally a dual function, especially the function as calibration resistor 56, on the one hand, and a function as dust cover for the coupling element on the output side 22 or as a dust cover for the HME filter 30, on the other hand.

Such a cover may optionally be provided together with the patient module 10, especially together with the patient module 10 in a package containing the patient module 10. Such a cover is shown in the view in FIG. 5 in a schematically simplified manner. As can be seen, the cover, which also acts as a calibration resistor 56, has a plurality of uniformly distributed holes. Flow through the cover is thus possible. A specific flow resistance and a fixed characteristic in relation to the input pressure and the volume flow are obtained because of the size and the number of holes.

In case of such a calibration resistor 56 with, for example, 50 openings each with 0.5 mm diameter in case of the mounting thereof at the or in the patient module 10 and with a ventilation pressure of 10 mbar being applied to the patient module 10, a typical volume flow of 30 L/min is obtained. A preset resistance factor (the factor "factor") is, for example, 0.3 mbar at 30 L/min. However, in case of a calibration process with the mounted calibration resistor 56, only a measured value, for example, of 0.27 mbar is obtained in case of the measurement of the pressure drop Δp over the particle filter 32. A linear correction is correspondingly calculated: 0.3 mbar/0.27 mbar=~1.11. If the resulting value as correction factor "factor" is inserted into the calculation term, then the result is Q=factor×correction×Δp=0.3 mbar/30 L/min×1.11×0.27 mbar=30 L/min at a ventilation pressure pinsp=10 mbar and a pressure drop of Δp=0.27 mbar over the particle filter 32. Thus, the volume flow actually flowing over the calibration resistor 56 under the given pressure conditions is obtained, and the pressure drop Δp determined over the particle filter 32 by means of the future use of the factors "factor" and "correction" can be converted into a volume flow Q in the calibrated state.

A calibration as described above—with a bag 50 acting as test volume or with a calibration resistor 56—usually and basically optionally takes place once before the use of a patient module 10. By means of the calibration, a volume flow determination optionally being carried out during the later use of the patient module 10 on the basis of the pressure drop over the particle filter 32 that can be determined by means of the sensor mechanism 42, 43 can be adapted in this manner to the concrete flow conditions through the particle filter 32, so that very accurate volume flow values are obtained. In addition or as an alternative, the calibration may—likewise basically optionally—also be carried out during the use of the patient module 10, especially during a brief interruption of the use of the patient module 10 during the ventilation of a patient. By means of the calibration, a volume flow determination optionally being carried out in case of the further use of the patient module 10 on the basis of the pressure drop over the particle filter 32, which pressure drop can be determined by means of the sensor mechanism 42, 43, can in this manner be adapted to the concrete and possibly dynamically changing flow conditions through the particle filter 32, so that very accurate volume flow values are obtained.

The calibration is carried out in an automated manner after mounting the bag 50 or the calibration resistor 56. The calibration is activated by means of an operating action at the patient module 10 or at the control module 34 associated with the patient module 10. For example, the actuation of a key or the like is considered to be an operating action. In the same way, the actuation of a key or the like of an operating unit in the form of a keyboard or of a mobile computer or the like, which operating unit can be temporarily connected to the patient module 10 or to the control module 34 is considered to be an operating action. The operating action starts the automated calibration. Within the framework thereof, a ventilation pressure curve 46 as in FIG. 3 or FIG. 4 is generated and the correction factor is determined in an automated manner on the basis of a pressure drop over the particle filter 32, which pressure drop results in case of the generated ventilation pressure curve 46.

The automated calibration is carried out according to a calibration process implemented in software and under the control of a corresponding computer program. The computer program is, for example, part of the mentioned control program that is executed during the operation of the patient module 10 by means of the processing unit of the control unit 40. The computer program may also be embodied as a separate computer program independent of the control program of the patient module 10. The computer program is executed upon activation of the calibration, for example, by means of the processing unit comprised by the control module 34. The value of the flow resistance over a wide range is largely independent of the respective active air pressure in a calibration resistor 56 in the form of a laminar resistor (many small openings). Higher dependences on the air pressure arise in case of a configuration as a turbulent resistor (diaphragm), because the measurement process in the operation is considered to be a laminar resistance ($\Delta p \sim Q \times \sqrt{\vartheta}$), while $\Delta p \sim Q2 \times \rho$ is applied in the turbulent case, where $\rho$ denotes the density of the flowing fluid and largely depends linearly on the active air pressure pabs and the local temperature $\vartheta$ (the density $\rho$ is proportional to the temperature $\vartheta$ and to the air pressure pabs).

With a dependence of $Q \sim \Delta p/\sqrt{\vartheta}$, changes in the ambient temperature lead to a constant error. If the temperature is known, this constant error can be compensated on the basis of this dependence, and such a compensation is optionally also provided in case of the patient module 10 being proposed here.

Figure 6:
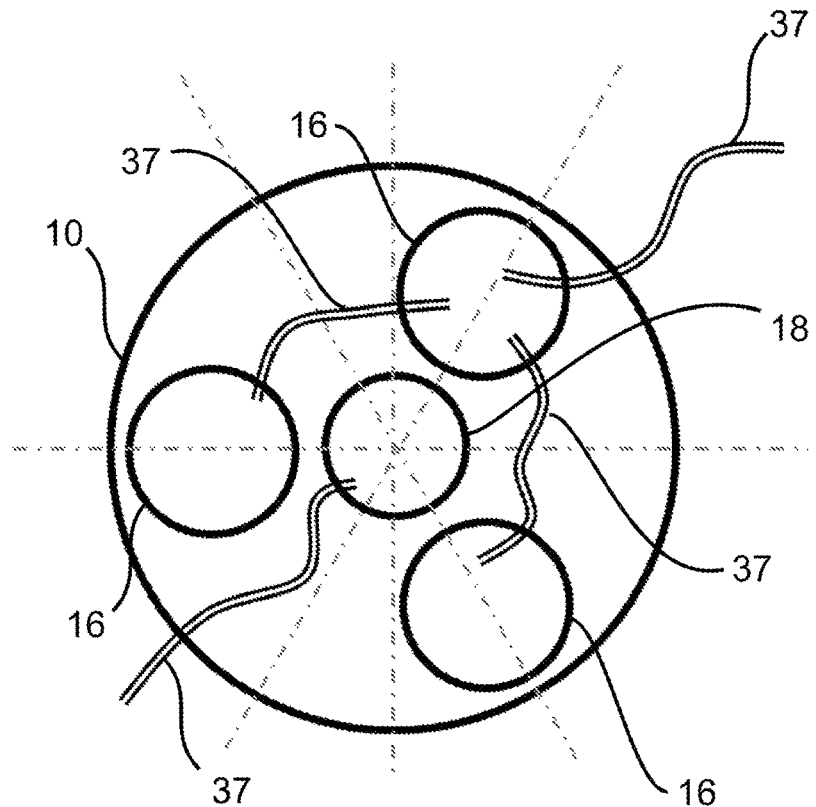
FIG. 6 is a schematic view showing an embodiment of the patient module with a plurality of exhalation valves.
Figure 7:
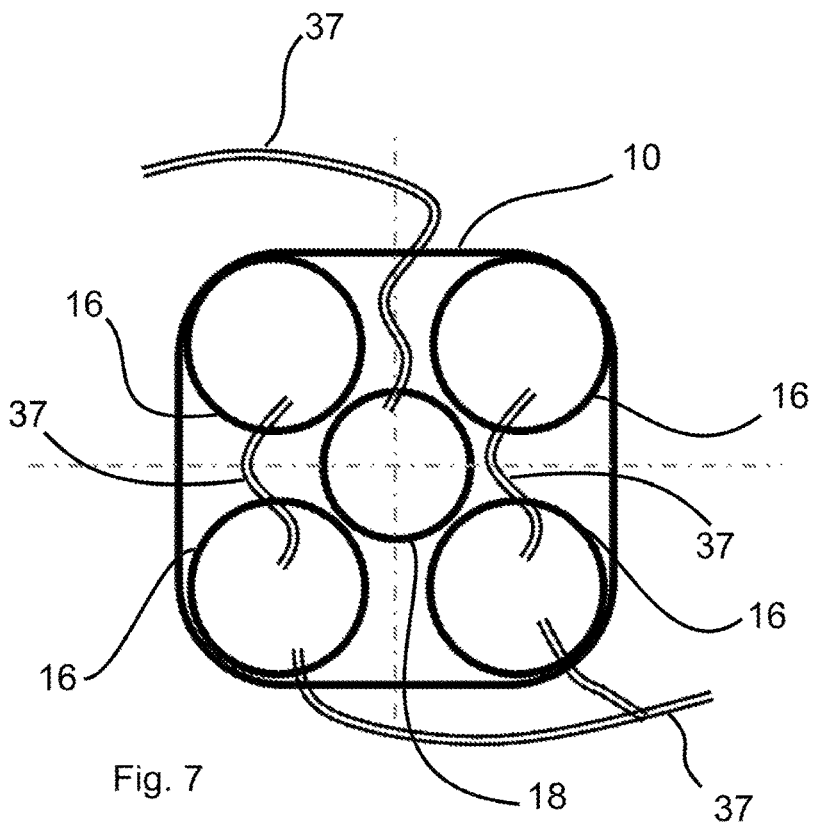
FIG. 7 is a schematic view showing an embodiment of the patient module with a plurality of exhalation valves.

The views shown in FIG. 6 and FIG. 7 show—each in a schematically highly simplified manner—embodiments of the patient module 10 with different numbers and with different placements of exhalation valves 16. In case of both embodiments being shown, the valves 16 enclose a centrally arranged inhalation valve 18. In case of the embodiment shown in FIG. 6, the patient module 10 comprises three exhalation valves 16 arranged along a circular line with their respective center at an angular distance of 120°. In case of the embodiment in FIG. 7, the patient module 10 comprises four exhalation valves 16 arranged along a circular line at an angular distance of 90°. The patient module 10 is characterized by a circular area in case of the embodiment shown in FIG. 6. In the embodiment shown in FIG. 7, the patient module 10 is characterized by an essentially square area (square with rounded corners). The embodiment with three exhalation valves 16 according to FIG. 6 may also be combined with an area of the patient module 10 according to FIG. 7 and vice versa. Generally, it is not a question of the number of the exhalation valves 16, so that more than four exhalation valves 16 and fewer than three exhalation valves 16 are conceivable as well. In principle, a special feature of an optional embodiment of the patient module 10 is expressed in the views in FIG. 6 and FIG. 7, especially of an embodiment with a larger number of exhalation valves 16 compared to the number of inhalation valves 18. In this respect, an embodiment with precisely one inhalation valve 18 and two or more exhalation valves 16 advantageously comes into consideration. The advantage in case of a higher number of exhalation vales 16 compared to the number of inhalation valves 18 is that the pressure drop over an inhalation valve 18 is relatively high (for example, 500 mbar), while the pressure drop over an exhalation valve 16 is low in relation thereto (for example, 20-30 mbar), so that a greater number of exhalation valves 16 reduces the flow resistance that is active during exhalation.

It can also be seen in the views in FIG. 6 and FIG. 7 that the control pressure chambers of the exhalation valves 16 are fluidically combined by means of corresponding tubes 37 in a basically optional manner. Such a fluidic combination makes possible an actuation of a plurality of exhalation valves 16 by means of a common valve drive 38, 39 (FIG. 1) and guarantees a uniform actuation of all exhalation valves 16 comprised by the patient module 10.

Figure 8:
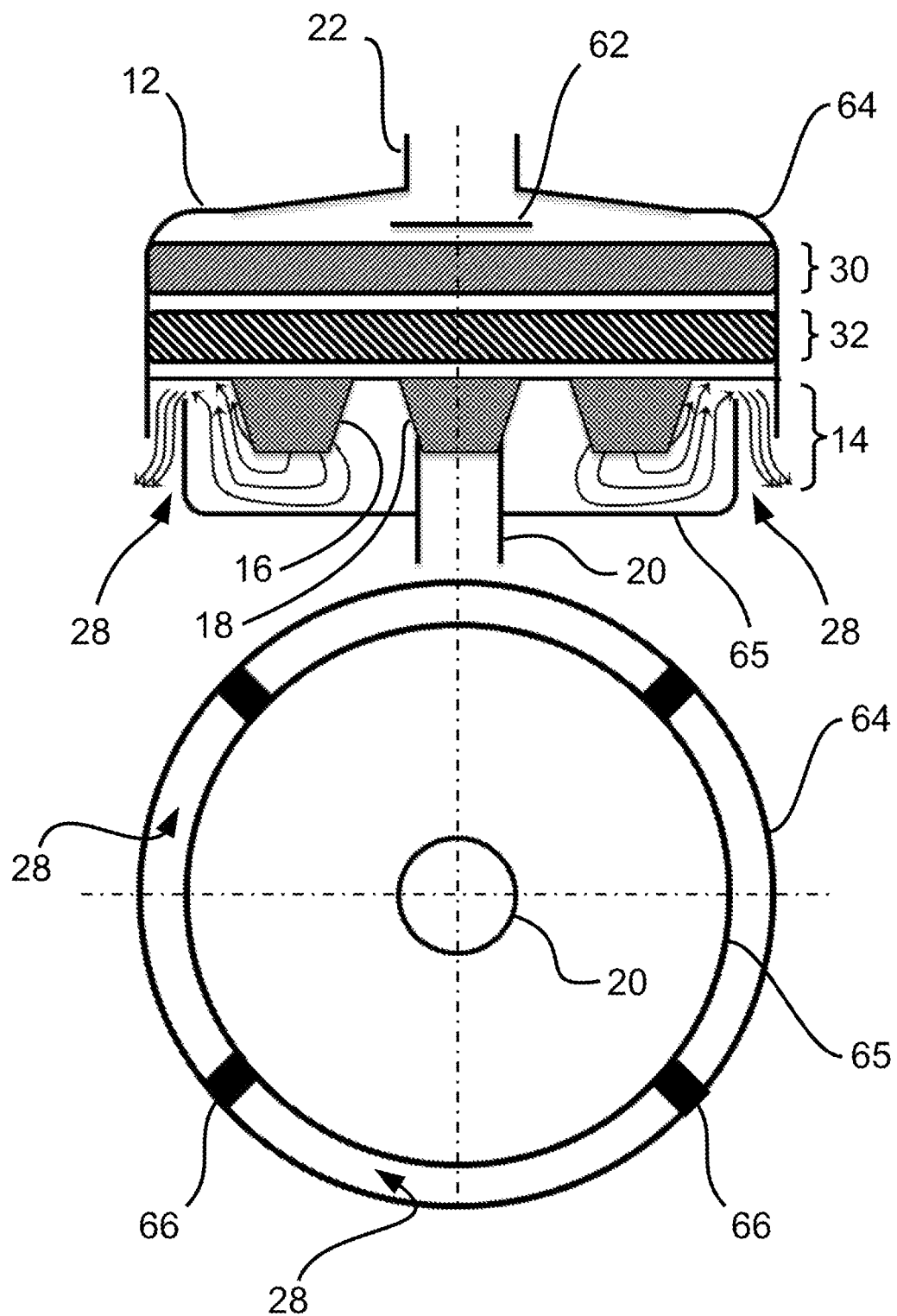
FIG. 8 is a schematic view showing one of different embodiments of a housing of the patient module for discharging breathing gas into the surrounding area.
Figure 9:
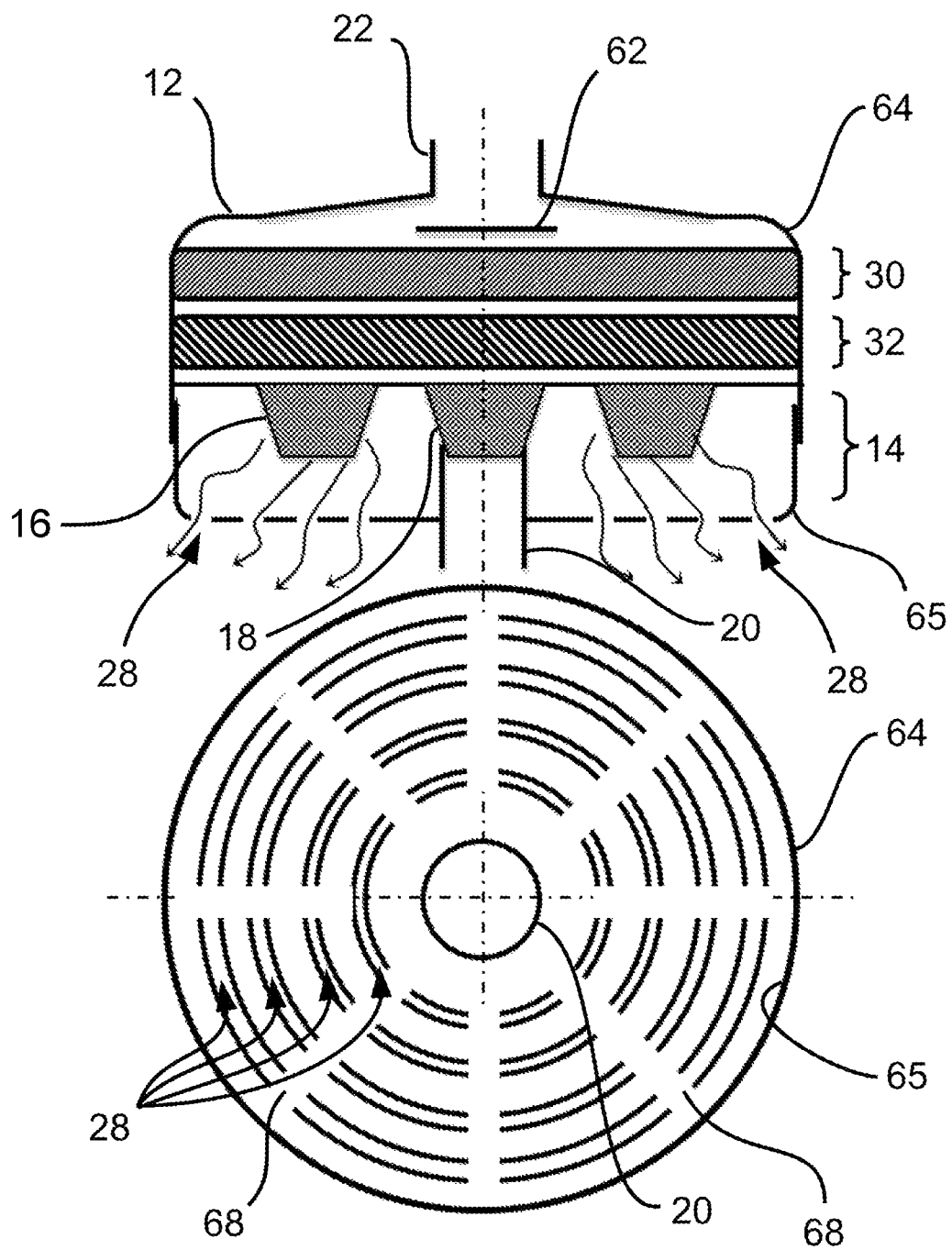
FIG. 9 is a schematic view showing one of different embodiments of a housing of the patient module for discharging breathing gas into the surrounding area.

The views in FIG. 8 and FIG. 9 show exemplary embodiments of the housing 12 of the patient module 10. The patient module 10 is shown in the upper area of each of the views in a sectional view and with a sectional plane as in FIG. 1. In the housing 12, an, in principle, optional impact surface 62 between the HME filter 30 and the coupling element on the output side 22 provides a not only central flow through the HME filter 30. The housing has at least two parts and comprises a housing upper part 64 and a housing lower part 65. The patient module 10 is shown in a viewing direction on the underside in the lower area of each of the views. Thus, the housing lower part 65 and the housing upper part 64 at the edge can be seen there. The coupling element on the input side 20 is located in the center of the area of the housing lower part 65 in the embodiments shown.

In the embodiment according to FIG. 8, the patient module 10 comprises a housing 12, in which a circumferential gap (ring-shaped outlet gap) remains as a housing opening 28 between the housing upper part 64 and the housing lower part 65. The exhaled breathing gas being released from the exhalation valve or each exhalation valve 16 during exhalation reaches the surrounding area through this housing opening 28—through the ring-shaped outlet gap. The curve of a corresponding air flow is shown in the upper area of the view in FIG. 8. The housing lower part 65 is connected to the housing upper part 64 by means of individual webs 66, for example, by means of a plurality of webs 66 distributed uniformly along a circumferential line of the patient module 10, wherein a free end of each web 66 meshes with a section of the inner surface of the housing upper part 64, which section is intended for this, for example, by locking into a corresponding counterprofile.

The embodiment of the housing 12 of the patient module 10 shown in FIG. 9 comprises this one housing lower part 65, in which the housing opening 28 is formed in the form of a plurality of concentric, ring-shaped outlet gaps, wherein individual spokes 68 connect the sections of the housing lower part 65 to one another, which sections remains between the outlet gaps. The housing lower part 65 is connected to the housing upper part 64, for example, by locking, especially by the housing lower part 65 meshing with a locking profile in a positive-locking manner with a corresponding counterprofile and a section of the inner surface of the housing upper part 64 that is intended for this.

Because of the divisibility of the housing 12, the housing lower part 65 may be removed from the housing upper part 64 (for example, by breaking corresponding locking connections). The valve section 14 is then accessible. The valves 16, 18 comprised by the valve section 14 are mounted on a common support plate and can be removed from the housing upper part 64 by removing the support plate. For this purpose, the support plate can be connected, for example, by locking to the inner surface of the housing upper part 64 in sections intended for this. After removal of the valve section 14, the particle filter 32 is accessible. This particle filter may now also be removed, for example, by breaking a locking connection with a corresponding section of the inner surface of the housing upper part 64, which locking connection is provided for the holding thereof. The HME filter 30 is also accessible after removal of the particle filter 32. This HME filter may now also be removed, for example, by breaking a locking connection with a corresponding section of the inner surface of the housing upper part 64, which locking connection is provided for the holding thereof. In this manner, the HME filter 30 and/or the particle filter 32 can be replaced. Because of the holding of the individual components (HME filter 30, particle filter 32, valve section 14) in the housing upper part 64, which can be established and broken by locking or otherwise without tools, the patient module 10 can be produced in a very simple manner by first the HME filter 30, then the particle filter 32 and finally the valve section 14 being placed and fixed in the housing upper part 64 and then the housing upper part 64 is closed by means of the housing lower part 65.

FIGS. 10 through 13 show further developments of the above-described embodiments of a patient module 10, in which the concrete configuration of the particle filter 32 is shown with additional details. According to these further developments, provisions are made for the particle filter 32 to be configured in the form of a filter assembly 32 and— corresponding to FIGS. 1a through 1e as well as FIGS. 8 and 9—to be arranged between the HME filter 30 and the valve section 14. FIG. 14 also shows such a further development, but with a different arrangement of the valve section 14. In this case, the valve section 14 (with at least one exhalation valve 16) may be arranged between the HME filter 30 and the particle filter 32, and the particle filter 32 may preferably be arranged between the valve section 14 and a valve assembly with at least one inhalation valve 18 (only suggested). The advantage can thus be obtained that the particle filter 32 is only used for the inspiratory volume flow 80, and thus the resistance during exhalation is reduced. For clarification, the inhalation gas 80 (i.e., also the inspiratory volume flow 80) and the exhalation gas 81 (i.e., also the expiratory volume flow 81) are shown by arrows.

The filter assembly 32 has at least two filter segments 71, 72, 73, 74 (especially separated from one another in substance and/or in space), so that the particle filter 32 provides its filtering through these filter segments 71, 72, 73, 74.

The valve section 14 is represented in FIGS. 10 through 14 by at least one valve 16, especially an exhalation valve 16, wherein the valve section 14 may, as an alternative or in addition, also have at least one inhalation valve 18 as described above (at least according to FIGS. 10 through 13). A variant (not shown) is also conceivable, in which the valve section 14 is dispensed with completely. In this case, the particle filter 32 in the form of the filter assembly 32 may be arranged between the HME filter 30 and the coupling element on the input side 20 described above.

The filter segments 71, 72, 73, 74 may each have a filter surface 75 (also designated as partial filter surface 75), which is in contact with the expiratory volume flow and/or with an inspiratory volume flow, which together form an overall surface in contact with the flow (also designated as overall filter surface).

Figure 10:
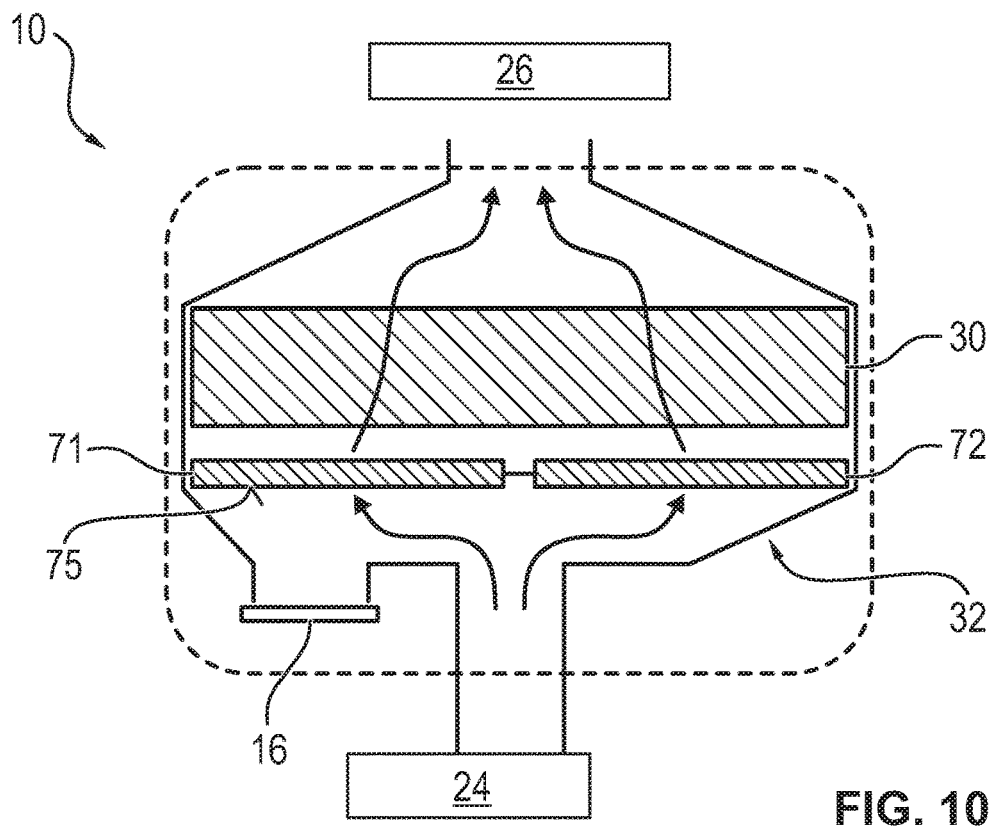
FIG. 10 is a schematic view showing an embodiment of a patient module with a particle filter, which has a plurality of filter segments.
Figure 11:
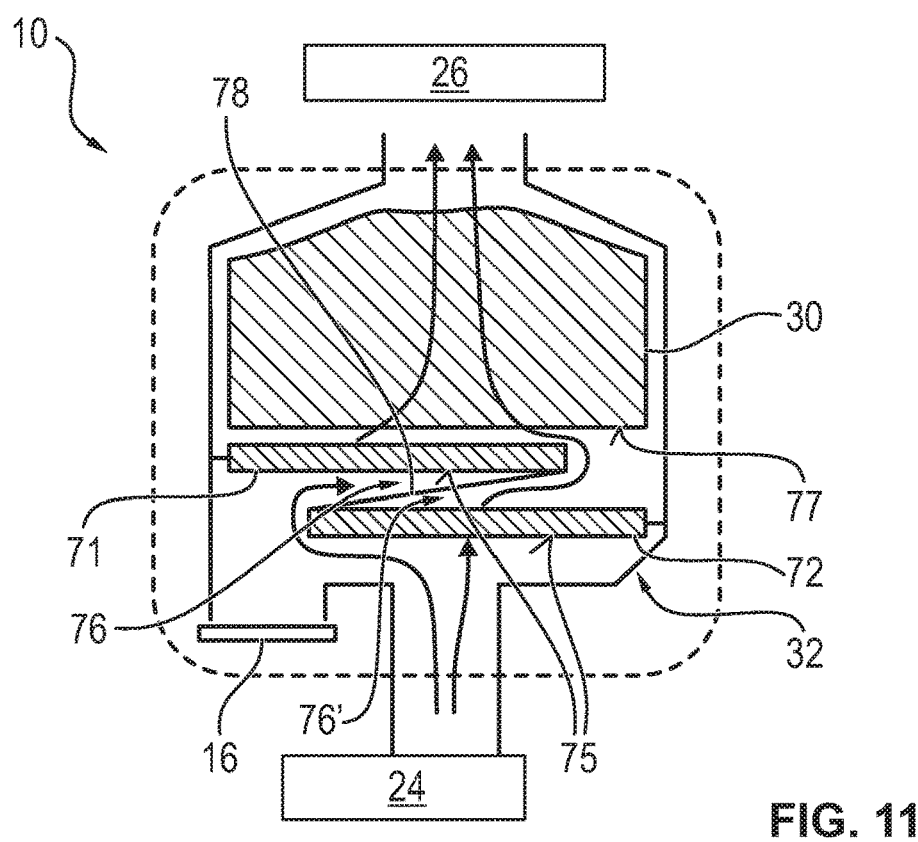
FIG. 11 is a schematic view showing an embodiment of a patient module with a particle filter, which has a plurality of filter segments.
Figure 12:
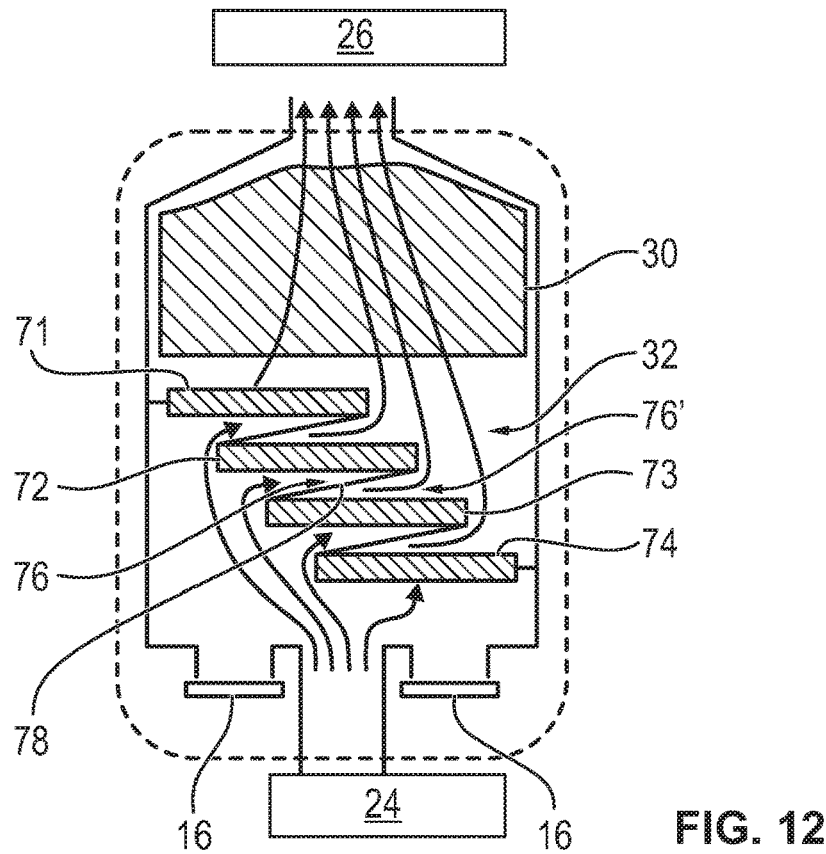
FIG. 12 is a schematic view showing an embodiment of a patient module with a particle filter, which has a plurality of filter segments.

The partial filter surface 75 of a first filter segment 71 is shown explicitly in FIG. 10. The first filter segment 71 and a second filter segment 72 are arranged next to one another in the flow path of the volume flow and are in this way arranged and/or aligned for the parallel flow of the respective volume flow through the respective filter surfaces 75. The parallel flow of the breathing gas during inhalation would correspondingly run in the opposite direction, i.e., from the HME filter 30 to the particle filter 32.

It is shown in FIGS. 11 through 14 that the filter segments 71, 72, 73, 74 are arranged spaced apart from one another, so that at least one flow space 76, 76' is formed between the filter segments 71, 72, 73, 74 in order for the volume flow to flow parallel through the filter surfaces 75 in the flow spaces 76, 76'. For this purpose, at least one separating device 78 is provided in order to separate facing filter surfaces 75 from one another in a fluid-tight manner, so that at least two flow spaces 76, 76' separated from one another are formed between the facing filter surfaces 75 to provide the flow in a parallel manner. Parallel flow refers here to the flow characteristic of the volume flow and not necessarily to the geometric arrangement that does not always have to be provided in a parallel manner to bring about the parallel flow.

Figure 13:
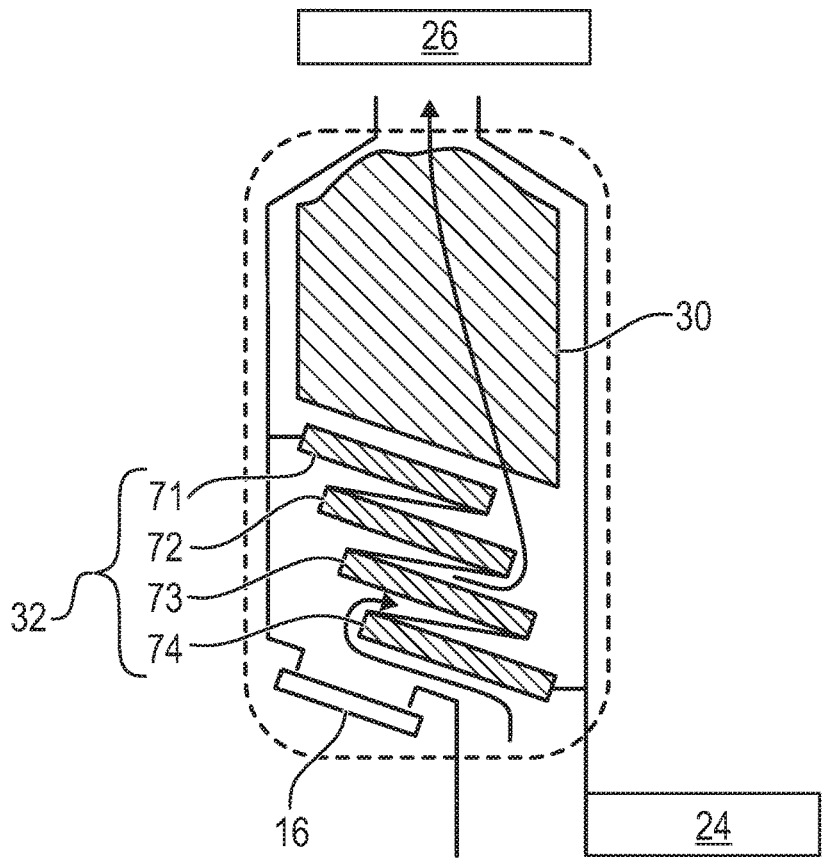
FIG. 13 is a schematic view showing an embodiment of a patient module with a particle filter, which has a plurality of filter segments.
Figure 14:
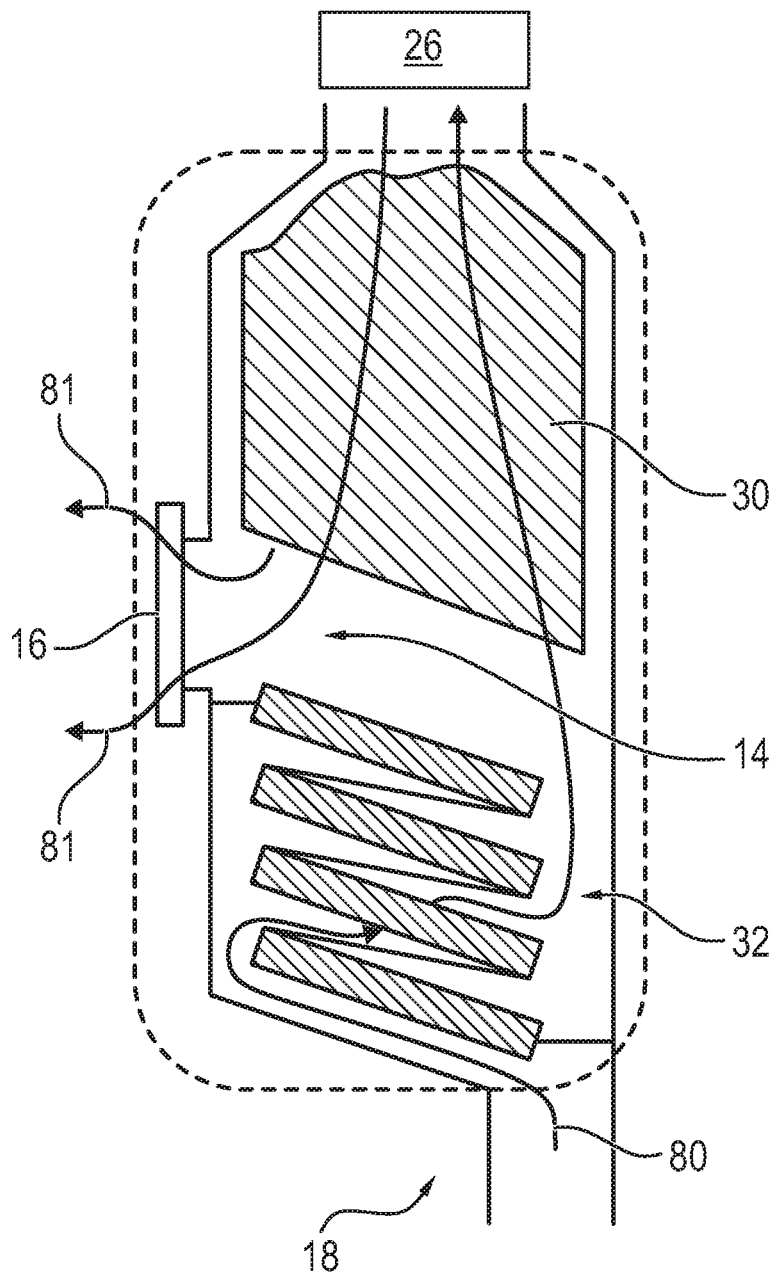
FIG. 14 is a schematic view showing an embodiment of a patient module with a particle filter, which has a plurality of filter segments.

The filter segments 71, 72, 73, 74 may be geometrically arranged behind one another—in relation to a flow direction of the volume flow (see FIGS. 11 through 14) and be aligned bent at an angle (see FIGS. 13 and 14). In this connection, a variant is shown, in which the filter segments 71, 72, 73, 74 have at least partially the same alignment bent at an angle, so that filter surfaces 75 of the filter segments 71, 72, 73, 74 are arranged parallel to one another. As an alternative, it is also possible that the filter segments 71, 72, 73, 47 at least partially have a different alignment bent at an angle.

Provisions are made in FIGS. 10 through 13 for the valve section 14 to have at least one exhalation valve 16, which has the same alignment bent at an angle as at least one of the filter segments 71, 72, 73, 74 bent at an angle, especially, e.g., the filter segment 74 located closest to the exhalation valve 16. Provisions are further made in FIGS. 10 through 14 for the HME filter 30 to have a surface 77 in contact with the flow, which surface is configured parallel to the filter surface 75 of at least one of the filter segments 71, 72, 73, 74 bent at an angle, preferably of the filter segment 71 located closest to the HME filter 30.

It is further shown that only one exhalation valve 16 (see FIGS. 10, 11, 13 and 14) or even two exhalation valves 16

(see FIG. 12) may be provided next to one another. However, it is also possible in case of the variant according to FIGS. 10, 11, 13 and 14 that at least or precisely two exhalation valves 16 are provided, or only one exhalation valve 16 is provided in the embodiment according to FIG. 12.

Some predominant aspects of the description being submitted here can thus be briefly summarized as follows: A patient module 10 intended for use during the ventilation of a patient is provided, wherein a pressure source 24 can be fluidically coupled by means of the patient module 10 to a patient interface 26, which can be connected to the airways of a patient, The patient module 10 comprises a housing 12 and a valve section 14 in the housing 12 as well as an HME filter 30 spaced apart from the valve section 14. The HME filter 30 is located upstream of the valve section 14 in relation to an expiratory volume flow, so that the HME filter 30 in the interior of the housing divides an interior space into a dry area and an area in contact with the moisture carried along by the exhaled breathing gas, and the valve section 14 is located in the dry area.

While specific embodiments of the invention have been shown and described in detail to illustrate the application of the principles of the invention, it will be understood that the invention may be embodied otherwise without departing from such principles.

| List of Reference Symbols | |
|---|---|
| 10 | Patient module |
| 12 | Housing (of the patient module) |
| 14 | Valve section (in the interior of the patient module) |
| 16 | Exhalation valve |
| 18 | Inhalation valve |
| 20 | Coupling element (on the input side) |
| 22 | Coupling element (on the output side) |
| 24 | Pressure source |
| 26 | Patient interface |
| 28 | Housing opening |
| 30 | HME filter |
| 32 | Particle filter |
| 34 | Control module |
| 36, 36' | Tube |
| 37, 37' | Tube |
| 40 | Control unit |
| 42, 43 | Sensor mechanism, pressure sensor |
| 44, 45 | Characteristic |
| 46 | Ventilation pressure curve |
| 48 | Pressure drop curve |
| 50 | Bag |
| 52 | Inverse volume flow |
| 54 | Area under the pressure drop measured value curve |
| 56 | Calibration resistor |
| 62 | Impact surface |
| 64 | Housing upper part |
| 65 | Housing lower part |
| 66 | Web |
| 68 | Spoke |
| 71-74 | Filter segment |
| 75 | Filter surface |
| 76, 76' | Flow space |
| 77 | Surface |
| 78 | Separating device |
| 80 | Inhalation gas |
| 81 | Exhalation gas |

What is claimed is:

1. A patient module for ventilating a patient, the patient module comprising:
    a central coupling element;
    a housing with an input connected to the central coupling element for fluidic connection of a pressure source and an output for fluidic connection to a patient interface, which can be connected to the airways of a patient to provide an inhalation volume flow path to the patient interface and an expiratory volume flow path from the patient interface, the housing comprising a housing inner surface defining at least a portion of an interior space of the housing;
    a valve section in the housing;
    a heat moisture exchange (HME) filter in the housing and spaced apart from the valve section, the HME filter being located upstream of the valve section in relation to an expiratory volume flow, the valve section comprising a plurality of exhalation valves located at or in the interior space of the housing, wherein all of the exhalation valves are arranged adjacent to the central coupling element.

2. A patient module in accordance with claim 1, wherein the plurality of exhalation valves comprises a first exhalation valve, a second exhalation valve and a third exhalation valve, each of the first exhalation valve, the second exhalation valve and the third exhalation valve being located at a same distance from the central coupling element, the central coupling element being aligned with a central axis of the housing, at least a portion of each of the exhalation valves being movable in a direction parallel to the central axis of the housing.

3. A patient module in accordance with claim 2, wherein:
    the valve section further comprises a central inhalation valve connected to the central coupling element; and
    the exhalation valves are arranged uniformly distributed about the central inhalation valve within the valve section.

4. A patient module in accordance with claim 1, wherein the valve section comprises at least one inhalation valve.

5. A patient module in accordance with claim 1, further comprising a particle filter arranged between the HME filter and the valve section, the plurality of exhalation valves being arranged uniformly distributed about the central coupling element, each of the exhalation valves being arranged at a spaced location from the housing inner surface.

6. A patient module in accordance with claim 5, further comprising a pressure sensor arranged at or adjacent to the HME filter, wherein a measured pressure value, which indicates an airway pressure, is acquired by means of the pressure sensor.

7. A patient module in accordance with claim 5, further comprising a first pressure sensor arranged in the patient module at or adjacent to the HME filter to obtain a first measured pressure value and a second pressure sensor in the patient module at or adjacent to the particle filter to obtain a second measured pressure value, to obtain a pressure difference which indicates quantities of gas flowing towards the patient or away from the patient.

8. A patient module in accordance with claim 5, further comprising a sensor mechanism arranged in the patient module at or adjacent to the particle filter and configured as a pressure difference sensor, wherein a pressure difference measured value, which indicates quantities of gas flowing towards the patient or away from the patient is acquired by means of the sensor mechanism.

9. A patient module in accordance with claim 5, further comprising a sensor mechanism arranged in the patient module at or adjacent to the HME filter and configured as a pressure difference sensor wherein a pressure difference measured value, which indicates quantities of gas flowing towards the patient or away from the patient, is acquired by means of the sensor mechanism.

10. A patient module in accordance with claim 5, wherein at least one pressure-measuring port is arranged at the HME filter, at the particle filter or at the valve section, the plurality of exhalation valves comprising a first exhalation valve, a second exhalation valve and a third exhalation valve, each of the first exhalation valve, the second exhalation valve and the third exhalation valve being located at a same distance from the central coupling element.

11. A patient module in accordance with claim 10, further comprising:
a first pressure sensor and a first tube; and
a second pressure sensor and a second tube, wherein:
an additional pressure-measuring port is arranged at the particle filter or at the valve section;
the additional pressure-measuring port is pneumatically connected to the second pressure sensor by means of the second tube;
the at least one pressure-measuring port is arranged at the HME filter or at the particle filter;
the at least one pressure-measuring port is pneumatically connected to the first pressure sensor by means of the first tube; and
two measured pressure values, the difference of which indicates quantities of gas flowing towards the patient or away from the patient, are acquired by means of the first pressure sensor and the second pressure sensor.

12. A patient module in accordance with claim 5, further comprising a sensor arrangement with a calibration means for determining a correction factor to obtain a calibrated volume flow value based on one of connecting a test volume to the patient module or based on a calibration resistor to determine a pressure drop over the particle filter determined by the sensor arrangement.

13. A patient module in accordance with claim 1, further comprising a filter assembly comprising a particle filter arranged between the HME filter and the valve section or comprising a particle filter with the valve section arranged between the HME filter and the particle filter, wherein the filter assembly comprises at least two filter segments.

14. A patient module in accordance with claim 13, wherein the filter segments are arranged behind one another and are aligned bent at an angle in relation to a flow direction of the volume flow.

15. A patient module in accordance with claim 14, wherein the filter segments have an at least partially different alignment bent at an angle.

16. A patient module in accordance with claim 14, wherein the filter segments have at least partially the same alignment bent at an angle, so that filter surfaces of the filter segments are arranged parallel to one another.

17. A patient module in accordance with claim 14, wherein the valve section has at least one exhalation valve, which has said alignment bent as at least one of the filter segments.

18. A patient module in accordance with claim 14, wherein the HME filter has a HME filter surface in contact with the flow, which HME filter surface is formed parallel to the filter surface of at least one of the filter segments of the filter segments that are bent at an angle.

19. A patient module in accordance with claim 13, wherein the filter segments are configured as separated in space from one another.

20. A patient module system comprising:
a patient module for ventilating a patient, the patient module comprising:
a central coupling element;
a housing with an input for fluidic connection of a pressure source and an output for fluidic connection to a patient interface, which can be connected to the airways of the patient to provide an inhalation volume flow path towards the patient interface and an expiratory volume flow path away from the patient interface, the central coupling element being connected to the input of the housing, the housing comprising a housing inner surface defining at least a portion of an interior space of the housing;
a valve section in the housing, the valve section comprising a plurality of exhalation valves, the plurality of exhalation valves being arranged in a middle area of the interior space between the central coupling element and an outer poltiuic the inner surface of the housing;
a heat moisture exchange (HME) filter in the housing and spaced apart from the valve section, the HME filter being located upstream of the valve section in relation to an expiratory volume flow; and
a particle filter arranged between the HME filter and the valve section; and
a control module that is separated in space from the patient module and is operably connected to the patient module, the control module comprising a sensor arrangement configured as a pressure difference sensor indicating quantities of gas flowing towards the patient or away from the patient.

21. A patient module system according to claim 20, wherein the control module further comprises an inhalation valve separated in space from the patient module, the plurality of exhalation valves being arranged uniformly distributed about the central coupling element, the control module being located at a spaced location from the housing, the plurality of exhalation valves being located at a spaced location from the inner surface of the housing.

22. A patient module in accordance with claim 20, wherein the plurality of exhalation valves comprises a first exhalation valve, a second exhalation valve and a third exhalation valve, each of the first exhalation valve, the second exhalation valve and the third exhalation valve being located at a same distance from the central coupling element, at least a portion of each of the exhalation valves being movable in a direction parallel to a longitudinal axis of the housing.

23. A process for the operation of a patient module comprising the steps of:
providing a patient module for ventilating a patient, the patient module comprising a central coupling element, a housing with an input connected to the central coupling element for fluidic connection of a pressure source and an output for fluidic connection to a patient interface, which can be connected to the airways of a patient to provide an inhalation volume flow path towards the patient interface and an expiratory volume flow path away from the patient interface, a valve section in the housing, a heat moisture exchange (HME) filter in the housing and spaced apart from the valve section, the HME filter being located upstream of the valve section in relation to an expiratory volume flow and a particle filter arranged between the HME filter and the valve section, the valve section comprising a plurality of exhalation valves, the housing comprising a housing inner surface defining at least a portion of an interior space of the housing, the plurality of exhalation valves being arranged in a middle area of the interior space between the central coupling element and the housing inner surface;

determining a pressure drop over the particle filter with a sensor arrangement configured as a pressure difference sensor;

determining a correction factor with a test volume or with a calibration resistor connected to the patient module; and weighting the determined pressure drop over the particle filter with the correction factor to obtain a calibrated volume flow value.

* * * * *